(12) United States Patent
Aletru et al.

(10) Patent No.: US 7,659,298 B2
(45) Date of Patent: Feb. 9, 2010

(54) PYRAZOLE DERIVATIVES AND USE THEREOF AS OREXIN RECEPTOR ANTAGONISTS

(75) Inventors: Michel Aletru, Paris (FR); Peter Aranyi, Budapest (HU); Maria Balogh, Dunakeszi (HU); Sandor Batori, Budapest (HU); Judit Bence, Budapest (HU); Philippe Bovy, Mareil Marly (FR); Zoltan Kapui, Budapest (HU); Endre Mikus, Budapest (HU); Claudie Namane, Villiers Inarne (FR); Christophe Philippo, Rueil (FR); Tibor Szabo, Budapest (HU); Zsuzsanna Tomoskozi, Budapest (HU); Katalin Urban-Szabo, Budapest (HU)

(73) Assignee: sanofi-aventis, Paris (FR)

( * ) Notice: Subject to any disclaimer, the term of this patent is extended or adjusted under 35 U.S.C. 154(b) by 326 days.

(21) Appl. No.: 11/425,583

(22) Filed: Jun. 21, 2006

(65) Prior Publication Data

US 2007/0021459 A1    Jan. 25, 2007

Related U.S. Application Data

(63) Continuation of application No. PCT/HU2004/000117, filed on Dec. 15, 2004.

(30) Foreign Application Priority Data

Dec. 22, 2003    (HU)    ..................................    0304101

(51) Int. Cl.
*A61K 31/4155*    (2006.01)
*A61K 31/44*    (2006.01)
*C07D 231/10*    (2006.01)
*C07D 401/14*    (2006.01)

(52) U.S. Cl. .................. 514/406; 548/356.1; 548/373.1; 548/375.1; 546/152; 546/268.1; 546/275.4; 544/224; 544/242; 544/284; 514/258.1; 514/314; 514/341

(58) Field of Classification Search .............. 548/356.1, 548/373.1, 375.1; 514/403, 406, 256, 258.1, 514/311, 314, 336, 341; 546/152, 268.1, 546/275.4; 544/224, 242, 284
See application file for complete search history.

(56) References Cited

U.S. PATENT DOCUMENTS 6,372,757 B1    4/2002    Johns et al.

OTHER PUBLICATIONS

Database Beilstein XP002329936, Accession No. BRN 5339747.
Database Beilstein XP002329937, Accession No. BRN 5338131.
Database Beilstein XP002329938, Accession No. BRN 518567.
Database Beilstein XP002329939, Accession No. BRN 8761301.
Database Beilstein XP002329940, Accession No. BRN 8762607.
Database Beilstein XP002329941, Accession No. BRN 533168.
Database Beilstein XP002329942, Accession No. BRN 799194.
Database Beilstein XP002329943, Accession No. BRN 677119.
Database Beilstein XP002329944, Accession No. BRN 750201.
Database Beilstein XP002329945, Accession No. BRN 9243846.

*Primary Examiner*—Golam M Shameem
(74) *Attorney, Agent, or Firm*—Brian R. Morrill

(57) ABSTRACT

The present invention relates to the orexin receptor antagonists compounds of the general formula (I) as well as to their isomers, salts and solvates, to the pharmaceutical compositions containing them and to the therapeutic application thereof.

11 Claims, No Drawings

PYRAZOLE DERIVATIVES AND USE THEREOF AS OREXIN RECEPTOR ANTAGONISTS

CROSS REFERENCE TO RELATED APPLICATIONS

This application is a continuation of International application No. PCT/HU2004/000,117, filed Dec. 15, 2004, which is incorporated herein by reference in its entirety; which claims the benefit of priority of Hungarian Patent Application No. P0304101, filed Dec. 22, 2003.

The present invention relates to the orexin receptor antagonist compounds of the general formula (I), as well as their isomers, salts and solvates, to the pharmaceutical compositions containing them and to the therapeutic application thereof.

Further subjects of the invention are the methods of preparation of the compounds of the general formula (I) and the new intermediates of these processes.

Orexines, in other name hypocretin neuropeptides and their receptors were discovered in 1998 by methods of molecular biology.

The orexinergic neuropeptides are formed in large amount in the neurons of the lateral hypothalamus, but via axonal transport processes, they also reach numerous remote areas of the nervous system. On the basis of experimental observations the orexinergic system seems to plays crucial role in the feeding, in the biological and circadian rhythms and in the regulation of the autonomic nervous system processes.

The orexin A and orexin B proteins are formed by the enzymatic cleavage of their only common precursor, the pre-proorexin protein molecule. Orexin A consists of 33 aminoacid residues with two intramolecular disulphide bridges. Orexin B is a linear protein consisting of 28 aminoacid residues. During the evolution of mammals the aminoacid sequence of the orexin peptides has largely been conserved. In man, pig, dog, mouse and rat species the aminoacid sequences of the orexin A peptides are fully identical, whereas the aminoacid sequences of the orexin B proteins differ only in a few aminoacids. The orexin-producing neurons of the brain form a heterogenous cell population: one part of them exhibits leptin sensitivity, whereas the other part glucose sensitivity.

Further subgroups of the orexinergic neurones are capable to express galanine, neuropeptide Y or dinorfine, in addition to the orexines.

The orexin A and orexin B bind to specific receptors on the surface of the target cells; i.e. the orexin-1 and orexin-2 receptors.

In men, the orexin-1 receptors consist of 425, whereas the orexin-2 receptors of 444 aminoacid residues, and their aminoacid sequences are in 64% identical. Between the variants of the two orexin receptor types occuring in the different mammal species (man, pig, dog, mouse, rat) a considerable sequence-homology (of 91-98%) can be found. The aminoacid sequence of the human orexin-1 receptor is in 94% identical with the aminoacid sequence of the rat, whereas the sequences of the human and rat orexin-2 receptors are in 95% identical.

The orexin A and B peptides bind with high affinity to both receptor types. Orexin affinities of the two receptor types were determined by intracellular $Ca^{2+}$ concentration measurements in recombinant systems (on CHO cells) and on hypothalamic neurons. Compared to the orexin B, the orexin A peptide was shown to be 10-50-fold more effective on the orexin-1 receptors, demonstrating that this receptor type is selective towards orexin A. On the orexin-2 receptors both neuropeptides exhibited similar, high activities, i.e. the orexin-2 receptors are not selective towards the orexin peptides. According to experimental results, the orexin-1 receptors—via the $G_{q/11}$ sub-class G-proteins—may activate the phosphiolipase β(PLCβ) enzyme, whereas the orexin-2 receptors are supposed to bind also to the $G_{q/11}$ and $G_{i/o}$ or $G_s$ sub-classess of the G-proteins, thus beside the PLCβ path, they may also influence the cAMP path. In the synaptic activity stimulating effect of the orexines a significant role may be played by their capability to evoke phosphorylation of the ion channels. The orexin-1 and 2 receptor types are most frequent in the central nervous system (brain, spinal marrow), but they can also be found in numerous peripherical tissue types (as for instance in the hypophysis, in the adrenal glands, in the gastro-intestinal tract, in the pancreas and in the kidney).

Orexines play important role in the regulation of the eating behaviour, the sleeping-awakening, cycle, the neuroendocrinological processes and in the complex regulation of the energy consumption. Orexines in the central nervous system get in interaction with a number of specific neuron-nuclea, as for instance with the feeding centres of the hypothalamus, with the sleep-awake centres in the brain stam, with the symphatic and parasymphatic neuron nuclea and with the limbic system. After ventricular administration, orexines enhance in a dose-dependent manner the food-intake, the length of the time of wakefullness, the motoric activity, the speed of the metabolic processes, the heart rhythm and the blood pressure. Latest electrophysiological studies have demonstrated that in the regulation of the functions of the orexin-producing neurons important mediators of the metabolic processes take part, such as the leptin, the glucose, the grelin, the monoamines and the acetylcholine, which means that the orexin-producing neurones develop functional connections with the feeding-centres, with monoaminerg-acetylcholinerg centres in the brain stem and with the factors reflecting the supply with food.

Orexins and their receptors can also be found in the peripheric tissues. Orexins exert a direct effect on the hypophysis and on the hormon secretion of the adrenal glands and they influence considerably the digestion and absorbtion processes acting locally, along the gastro-intestinal tract.

The orexin-A can effectively increase both in vitro and in vivo the insuline secretion of the pancrease and the leptin secretion of the lipides.

These observations prove that the orexinergic neuropeptides and their receptors play important role in the energy intake—expenditure balance and in the higher regulation of the adaptive behavioural processes.

Based on the above, we can expect that compounds exerting antagonistic effect on the orexin-2 and orexin-2 receptors are suitable—among others—to treat diseases like obesity, including obesity of the non-insulin-dependent diabetes patients, for the treatment of sleeping disorders, stroke, nausea and vomiting.

We aimed to prepare novel compounds suitable for drug development, exerting strong antagonistic effect on the orexin-1 and orexin-2 receptors, first of all on the orexin-1 receptors.

We have found that the compounds of the general formula (I) wherein

Ar represents phenyl group or a 5- or 6-membered heteroaromatic ring containing 1-3 heteroatoms, preferably nitrogen atom, oxygen atom or sulphur atom, where any of these rings may optionally be mono- or polysubstituted with halogen atom, $C_{1-4}$ alkyl group, $C_{1-4}$ alkoxy group, hydroxyl group, cyano group, trihalogenomethyl group, amino group or an amino group substituted with one or two $C_{1-4}$ alkyl group;

Y stands for —$CH_2$— group,

X stands for sulphur atom, oxygen atom, —NH-group, —N($C_{1-4}$ alkyl) group, —$CH_2$-group, —(S=O)— or —$SO_2$-group or X and Y together represent a —CH=CH- group with cis or trans geometry, A represents a moiety with a five- or six-membered aromatic ring which contains in ortho-, meta- or para-position two free valencies, and is optionally mono- or polysubstituted with halogen atom, $C_{1-4}$ alkyl group or $C_{1-4}$ alkoxy group; or with a partially or fully saturated five- or six-membered cycloalkyl ring optionally mono- or polysubstituted with halogen atom, $C_{1-4}$ alkyl group or $C_{1-4}$ alkoxy group; or with a heteroaromatic or partially or fully saturated heterocyclic ring wich contains 1-3 heteroatoms, preferably nitrogen, oxygen or sulphur atom, and is optionally mono- or polysubstituted with halogen atom, $C_{1-4}$ alkyl group or $C_{1-4}$ alkoxy group;

$R^1$ represents benzyl group, $C_{1-4}$-alkyl-, $C_{1-4}$-hydroxyalkyl-, $C_{3-8}$-alkoxycarbonylalkyl-, $C_{2-7}$-alkylcarbonyl-, $C_{2-7}$-carboxyalkyl-, aminocarbonyl-($C_{1-4}$)-alkyl, $C_{1-3}$-alkylaminocarbonyl-($C_{1-4}$)-alkyl, amino-($C_{1-4}$)-alkyl, $C_{1-3}$-alkylamino-($C_{1-4}$)-alkyl-, morpholino-($C_{1-4}$)-alkyl-, or morpholinocarbonyl-($C_{1-4}$)-alkyl group or a phenyl group, optionally substituted with one or more halogen atoms, $R^2$ represents one of the following groups which is optionally substituted with one or more halogenatom, hydroxyl group, $C_{1-4}$ alkyl group, trihalogenomethyl-group, thio-$C_{1-4}$-alkyl group, amino group, —(C=O)—NH—$C_{1-4}$-alkyl or cycloalkyl group: phenyl group, phenylethyl group, naphthyl group, indanyl- or indenyl group, five- or six-membered heteroaromatic or partially or fully saturated cyclic group containing 1-3 identical or different heteroatoms, preferably nitrogen, oxygen or sulphur atom, a group containing a bicyclic heteroaromatic moiety or a partially or fully saturated bicyclic heteroring with 1 or 2 or 3 identical or different heteroatoms, preferably nitrogen, oxygen or sulphur atom;

$R^3$ stands for hydrogen atom or $C_{1-4}$ alkyl group, $R^2$ and $R^3$ together with the nitrogen atom to which they are attached may represent a partly or fully saturated six-membered ring optionally substituted with a substituted phenyl or benzyl group.

$R^5$ stands for halogen atom, hydrogen atom, $C_{1-4}$ alkyl group, $C_{1-4}$ thioalkyl group, $C_{1-4}$ alkoxy group— and their salts, isomers, and solvates exert significant orexin-1 and orexin-2 receptor antagonistic activity, first of all orexin-1 antagonistic activity and they are suitable for drug development.

One favourable group of compounds of the above family are those of the general formula (I) wherein Ar stands for phenyl group or a 6-membered heteroaromatic ring with 1 or 2 nitrogen atoms, where the aromatic rings may optionally be mono- or polysubstituted with halogen atom or $C_{1-4}$ alkoxy group, Y stands for methylene group, X stands for sulphur atom, oxygen atom, methylene group, —N(methyl) group;

A represents ortho-phenylene group or a heteroaromatic moiety containing in ortho-position two free valencies;

$R^1$ represents $C_{1-4}$-alkyl-, $C_{1-5}$-hydroxyalkyl-, $C_3$-s-alkoxycarbonylmethyl, $C_{2-6}$-carboxyalkyl- or methylaminocarbonyl group, or an alkylaminocarbonyl group substituted with one or two $C_{1-4}$-alkyl group;

$R^2$ represents aromatic or partially saturated bicyclic group containing 0, 1, 2 or 3 heteroatoms, optionally substituted with one or more $C_{1-4}$-alkyl group, halogen atom or amino group, $R^3$ represents hydrogen atom, $R^5$ represents halogen atom, $C_{1-4}$-alkyl-, or $C_{1-4}$-alkylthio group, An especially favourable compounds of the general formula (I) are wherein Ar represents a phenyl group, optionally substituted with halogen atom; or a 6-membered heteroaromatic ring with 1 or 2 nitro-en atoms, optionally substituted with halogen atom, Y stands for methylene group, X represents methylene group, sulphur atom, oxygen atom, or a nitrogen atom carrying a $C_{1-4}$-alkyl group;

A represents ortho-phenylene group or a heteroaromatic moiety containing in ortho-position two free valencies;

$R^1$ represents a staight or branched $C_{1-4}$ alkyl group, $C_{1-3}$ hydroxyalkyl group or $C_{3-6}$ alkoxycarbonylmethyl group;

$R^2$ represents an aromatic or partially saturated bicyclic moiety optionally substituted with $C_{1-4}$ alkyl group or halogen atom; or an aromatic or partially saturated bicyclic moiety containing 1-3 heteroatoms, favourably nitrogen, sulphur or oxygen atom, $R^3$ represents hydrogen atom, $R^5$ represents chloro atom, methyl group or thiomethyl group.

By $C_{1-4}$ alkyl group we mean a straight or branched carbon chain, such as for instance the methyl, ethyl, n-propyl or isopropyl group, or the different butyl groups, By $C_{1-4}$ alkoxy group we mean a straight or branched carbon chained group, as for example the methoxy, ethoxy, n-propoxy or isopropoxy group, or the different butoxy groups.

By halogen atom we mean a fluoro, chloro, bromo or iodo atom.

By trihalogenomethyl group we mean a methyl group substituted with 3 identical or different halogen atoms, for example a trifluoromethyl- or trichloromethyl group.

The five- or six-membered heteroaromatic ring may for example be a thiofen, furan, pyrrole, imidazole, pyrazole, pyrazine, pyrimidine, pyridazine or pyran ring.

The bicyclic heteroaromatic ring may for example be a quinoline, isoquinoline, quinoxaline, quinazoline, benzthiazine or benzodiazine ring.

Far from beeing complete, herebelow we list some of the most important compounds of the general formula (I) according to the invention:

2-(3-Phenyl-5-chloro-1-methyl-1H-pyrazol-4-ylmethylsulphanyl)-N-quinolin-3-ylbenzamide;

2-(3-Phenyl-5-chloro-1-methyl-1H-pyrazol-4-ylmethylsulphanyl)-N-naphthalin-2-ylbenzamide;

2-(3-Phenyl-5-chloro-1-methyl-1H-pyrazol-4-ylmethylsulphanyl)-N-quinolin-6-ylbenzamide hydrochloride;

2-(3-Phenyl-5-chloro-1-methyl-1H-pyrazol-4-ylmethylsulphanyl)-N-indan-5-ylbenzamide;

2-(5-Chloro-1-methyl-3-pyridin-2-yl-1H-pyrazol-4-ylmethylsulphanyl)-N-naphthalin-2-ylbenzamide;

2-(5-Chloro-1-methyl-3-pyridin-2-yl-1H-pyrazol-4-ylmethylsulphanyl)-N-quinolin-3-ylbenzamide;

2-(5-Chloro-1-methyl-3-pyridin-3-yl-1H-pyrazol-4-ylmethylsulphanyl)-N-naphthalin-2-ylbenzamide;

2-(5-Chloro-1-methyl-3-pyridin-3-yl-1H-pyrazol-4-ylmethylsulphanyl)-N-quinolin-6-ylbenzamide;

2-(5-Chloro-1-methyl-3-pyridin-3-yl-1H-pyrazol-4-ylmethylsulphanyl)-N-quinolin-3-ylbenzamide;

N-(1-Bromoisoquinolin-3-yl)-2-(5-chloro-1-methyl-3-pyridin-3-yl-1H-pyrazol-4-ylmethylsulphanyl)benzamide;
2-(5-Chloro-1-methyl-3-pyridin-3-yl-1H-pyrazol-4-ylmethylsulphanyl)-N-isoquinolin-3-ylbenzamide;
2-(5-Chloro-1-methyl-3-pyridin-4-yl-1H-pyrazol-4-ylmethylsulphanyl)-N-naphthalin-2-ylbenzamide;
2-(5-Chloro-1-methyl-3-pyridin-4-yl-1H-pyrazol-4-ylmethylsulphanyl)-N-quinolin-3-ylbenzamide;
2-(5-Chloro-1-methyl-3-pyridin-4-yl-1H-pyrazol-4-ylmethylsulphanyl)-N-quinolin-6-ylbenzamide;
2-(5-Chloro-1-methyl-3-pyrazin-2-yl-1H-pyrazol-4-ylmethylsulphanyl)-N-quinolin-3-ylbenzamide;
2-(5-Chloro-1-methyl-3-pyridin-4-yl-1H-pyrazol-4-ylmethylsulphanyl)-N-(1-methylisoquinolin-3-yl)benzamide;
2-(1-Ethyl-3-phenyl-5-chloro-1H-pyrazol-4-ylmethylsulphanyl)-N-quinolin-3-ylbenzamide;
2-(3-Phenyl-5-chloro-1-propyl-1H-pyrazol-4-ylmethylsulphanyl)-N-quinolin-3-ylbenzamide;
2-(1-Butyl-3-phenyl-5-chloro-1H-pyrazol-4-ylmethylsulphanyl)-N-quinolin-3-ylbenzamide;
Ethyl-{3-phenyl-5-chloro-4-[2-(quinolin-3-ylcarbamoyl)-phenysulphanylmethyl]-1H-pyrazol-1-yl}-acetate;
2-[3-Phenyl-1-(2-hydroxyethyl)-5-chloro-1H-pyrazol-4-ylmethylsulphanyl]-N-quinolin-3-ylbenzamide;
2-(3-Phenyl-1,5-dimethyl-1H-pyrazol-4-ylmethylsulphanyl)-N-quinolin-3-ylbenzamide;
2-(3-Phenyl-1-methyl-5-methylsulphanyl-1H-pyrazol-4-ylmethylsulphanyl)-N-quinolin-3-ylbenzamide;
3-(3-Phenyl-5-chloro-1-methyl-1H-pyrazol-4-ylmethylsulphanyl)-thiophen-2-carboxylic acid naphthalin-2-ylamide;
2-(3-Phenyl-5-chloro-1-methyl-1H-pyrazol-4-ylmethoxy)-N-quinolin-3-ylbenzamide;
2-(3-Phenyl-5-chloro-1-methyl-1H-pyrazol-4-ylmethoxy)-N-naphthalin-2-ylbenzamide;
2-(5-Chloro-1-methyl-3-pyridin-3-yl-1H-pyrazol-4-ylmethoxy)-N-quinolin-3-ylbenzamide;
2-(5-Chloro-1-methyl-3-pyridin-4-yl-1H-pyrazol-4-ylmethoxy)-N-quinolin-3-ylbenzamide;
2-(5-Chloro-1-methyl-3-pyridin-2-yl-1H-pyrazol-4-ylmethoxy)-N-quinolin-3-ylbenzamide;
2-[3-(4-Fluorophenyl)-5-chloro-1-methyl-1H-pyrazol-4-ylmethoxy]-N-quinolin-3-ylbenzamide;
2-[2-(3-Phenyl-5-chloro-1-methyl-1H-pyrazol-4-yl)ethyl]-N-quinolin-3-ylbenzamide;
2-[2-(5-Chloro-1-methyl-3-pyridin-3-yl-1H-pyrazol-4-yl)ethyl]-N-quinolin-3-ylbenzamide;
2-[(3-Phenyl-5-chloro-1-methyl-1H-pyrazol-4-ylmethyl)methylamino]-N-quinolin-3-ylbenzamide;
2-(5-Chloro-1-methyl-3-pyridin-4-yl-1H-pyrazol-4-ylmethylsulphanyl)-N-(3,4-dichlorophenyl)benzamide;
2-[5-Chloro-1-methyl-3-(2-thienyl)-1H-pyrazol-4-ylmethoxy]-N-quinolin-3-ylbenzamide;
2-[(5-Chloro-1-methyl-3-pyridin-3-yl-1H-pyrazol-4-yl methyl)methylamino]-N-quinolin-3-ylbenzamide;
2-(5-Chloro-1-methyl-3-pyridin-3-yl-1H-pyrazol-4-ylmethoxy)-N-(6,7-difluoroquinolin-3-yl)benzamide;
2-(5-Chloro-1-methyl-3-pyridazin-3-yl-1H-pyrazol-4-ylmethoxy)-N-quinolin-3-ylbenzamide;
2-(5-Chloro-1-methyl-3-pyridazin-4-yl-1H-pyrazol-4-ylmethoxy)-N-quinolin-3-ylbenzamide.

The $IC_{50}$ values for the antagonistic effect of the compounds of the general formula (I) are usually smaller than 1000 nM, the favourable compounds exhibit on the orexin receptor $IC_{50}$ values which are smaller than 100 nM.

For demonstration herebelow we give $IC_{50}$ values of three of our compounds of the general formula (I):

2-(3-Phenyl-5-chloro-1-methyl-1H-pyrazol-4-ylmethlylsulphanyl)-N-naphthalin-2-ylbenzamide Orex-1 $IC_{50}$ 33 nM, Orex-2 $IC_{50}$ 156 nM 2-(5-Chloro-1-methyl-3-pyridin-4-yl-1H-pyrazol-4-ylmethoxy)-N-quinolin-3-ylbenzamide Orex-1 $IC_{50}$ 51 nM, Orex-2 $IC_{50}$ 1100 nM 2-[2-(5-Chloro-1-methyl-3-pyridin-3-yl-1H-pyrazol-4-yl)ethyl]-N-quinolin-3-ylbenzamide Orex-1 $IC_{50}$ 57 nM, Orex-2 $IC_{50}$ 680 nM FIGS. 1 and 2 demonstrate the processes for the preparation of the compounds of the general formula (I). According, to the first process the acid of the general formula (II)—where in the formula Ar, Y, X, A, $R^1$, and $R^5$ have the same meanings as defined above—is transformed with an acid halogenide-forming agent, preferably with thionyl chloride into the acid chloride, which is then reacted with the amine of the general formula (III)—where in the formula $R^2$ and $R^3$ have the same meanings as defined above—in an inert solvent (e.g. dichloromethane, chloroform, ethyl acetate, in the presence of a base (e.g. triethylamine) or in pyridine, at room temperature or at the reflux temperature of the reaction mixture.

According to another embodient the acid of the general formula (II)—where in the formula Ar, Y, X, A, $R^1$, and $R^5$ have the same meanings as defined above—is reacted with the amine of the general formula (III)—where in the formula $R^2$ and $R^3$ have the same meanings as defined above—in the presence of an activating agent. The activating agent may be the 1-ethyl-3-(3'-dimethylaminopropyl)carbodiimide (EDC) or 4-(4,6-dimethoxy-1,3,5-triazine-2-yl)-4-methylmorpholinium chloride (DMTMM) or benzotriazol-1-yloxy-tris-pyrrolidinophosphonium-hexafluorophosphate (PyBOP). The reaction is carried out in an inert solvent (e.g. N,N-dimethylformamide, dichloromethane, tetrahydrofuran, dioxane), at room temperature or at the reflux temperature of the reaction mixture.

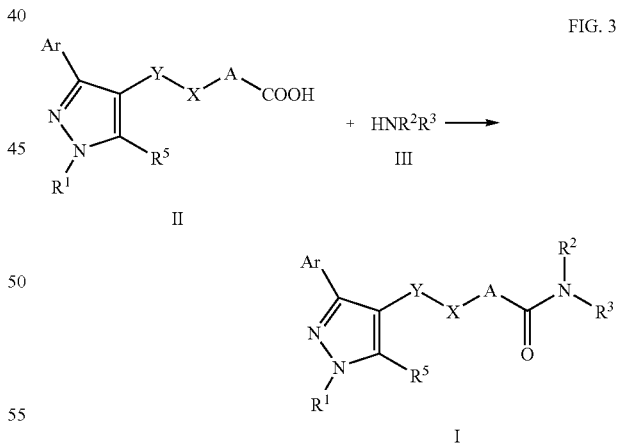

FIG. 3

In another process the compound of the general formula (VI)—where in the formula Ar, $R^1$, and $R^5$ have the same meanings as defined above—is reacted with the amid of the general formula (IX)—where in the formula X, A, $R^2$ and $R^3$ have the same meanings as defined above—in the presence of a base, (e.g. potassium carbonate, cesium carbonate) in an inert solvent (e.g. acetone, acetonitrile, ethanol, N,N-dimethylformamide) at room temperature or at the reflux temperature of the reaction mixture. (FIG. 2)

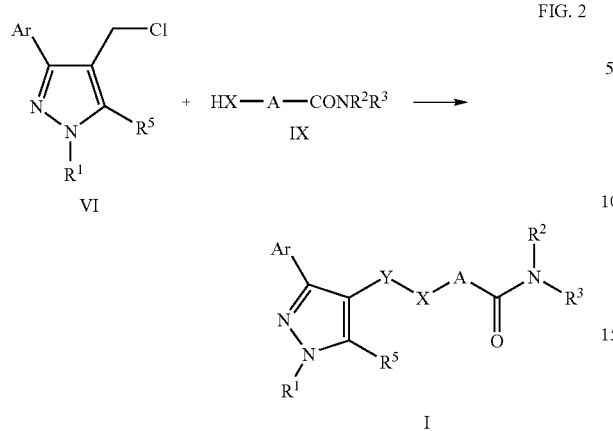

FIG. 2

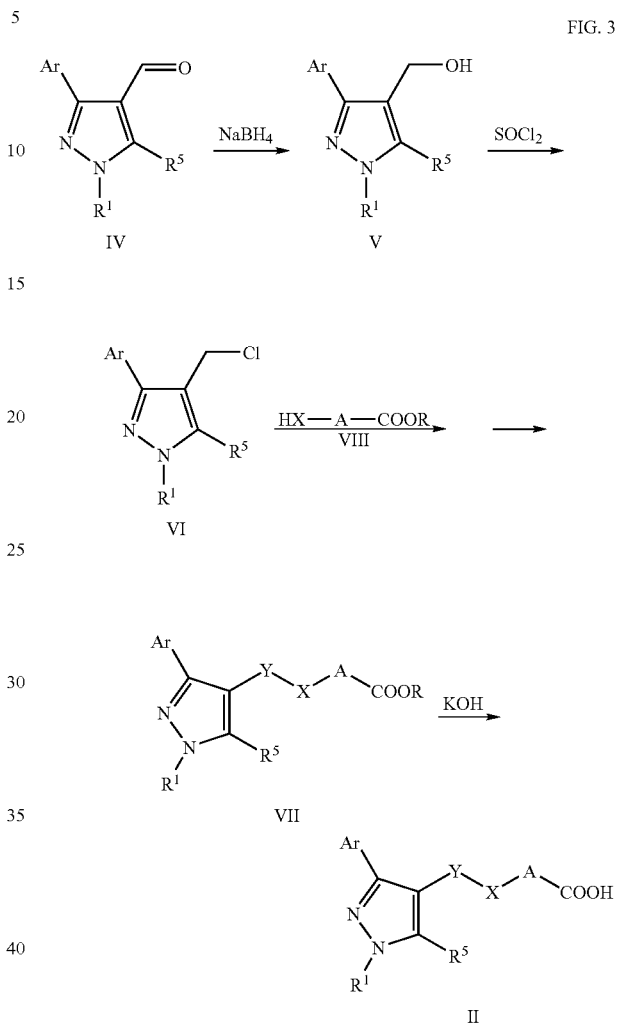

FIG. 3

The functional groups of the compound of the general formula (I) may be transformed into other functional groups (e.g. the $R^1$ or $R^3$ substituent into another $R^1$ or $R^3$ substituent).

The compound of the general formula (IV)—where in the formula Ar represents phenyl group, $R^1$ represents methyl group and $R^5$ represents chloro atom—is known from the literature. (J. Org. Chem. 1992, 57, 2127), further compounds of the general formula (IV)—where in the formula Ar, $R^1$, and $R^5$ have the same meanings as defined above—can be prepared by methods known from the literature. (See Table 11.). The compounds of the general formulae (V), (VI) and (II)—where in the formula Ar represents phenyl group, $R^1$ represents methyl group, $R^5$ represents chloro atom, X represents sulphur atom and A represents phenyl group to which the sulphur atom and the carboxy group is attached in ortho-position, are available on the market. Further compounds of the general formula (VI), (VII) and (II)—where in the formula Ar, $R^1$, $R^5$ X and A have the same meanings as defined above—are novel, not known from the literature, they can be prepared by the sequence of reactions shown in FIG. 3 (See Table 12-15.). Reduction of the compounds of the general formula (IV) may be realized by sodium borohydride in ethanol, chlorination of the compounds of the general formula (V) is performed by using thionyl chloride in an inert solvent (dichloromethane, or chloroform). The compound of the general formula (VIII),—where in the formula X and A have the same meanings as defined above and R stands for hydrogen or $C_{1-4}$ alkyl group—is alkylated with the compound of the general formula (VI)—where in the formula Ar, $R^1$ and $R^5$ have the same meanings as defined above—in the presence of a base (e.g. potassium carbonate, cesium carbonate, triethylamine), in a suitable solvent (e.g. ethanol, N,N-dimethylformamide, acetone, acetonitrile, dichloromethane, chloroform). The compound of the general formula (VII)—where in the formula Ar, $R^1$, $R^5$, Y, X and A have the same meanings as defined above and R stands for $C_{1-4}$ alkyl group—is hydrolyzed with sodium hydroxide or potassium hydroxide in aqueous ethanol into the compound of the general formula (II)—where in the formula Ar, $R^1$, $R^5$, Y, X and A have the same meanings as defined above. (See Table 13-14.)

The compounds of the general formula (II)—where in the formula Ar, $R^1$, $R^5$, and A have the same meanings as defined above, X and Y stand for CH) group or Y and X form together a —CH=CH-group—can be prepared by the sequence of reactions shown in FIG. 4.

The compound of the general formula (VI)—where in the formula Ar, $R^1$, and $R^5$, have the same meanings as defined above—is reacted with triphenylphosphine in an inert solvent (e.g. toluene, xylene) at the reflux temperature of the reaction mixture. The phosphonium salt of the general formula (X)—where in the formula Ar, $R^1$, and $R^5$, have the same meanings as defined above—is reacted in the presence of a base (e.g. sodium hydride) in N,N-dimethylformamide with the compound of the general formula (XI)—where in the formula A has the same meanings as defined above and R stands for $C_{1-4}$ alkyl group. The ester of the general formula (VII)—where in the formula Ar, R, $R^1$, $R^5$ and A have the same meanings as defined above—is hydrolyzed in alkaline medium and the resulting acid (II) is hydrogenated in ethanol, in the presence of Pd/C catalyst.

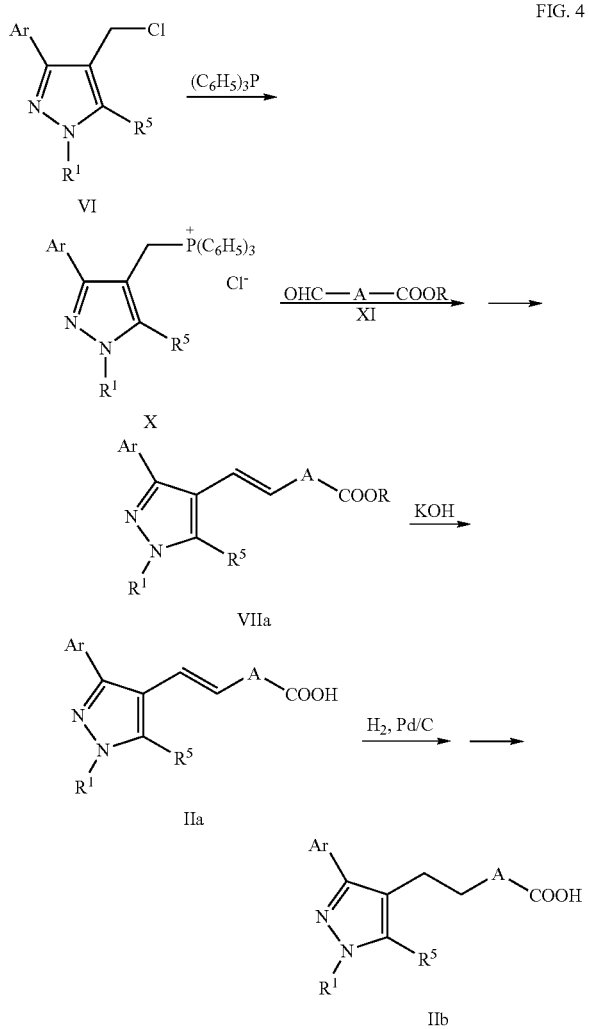

FIG. 4

In FIG. 4 by general formula (VIIa) we mean a general formula (VII) where Y and X form together a —CH═CH— group;

by general formula (IIa) we mean a general formula (II) where Y and X form together a —CH═CH— group;

by general formula (IIb) we mean a general formula (II), where Y represents a —CH$_2$— group, X represents a —CH$_2$— group.

The pharmaceutically acceptable salts of the compounds of the general formula (I) can be prepared by reacting the bases with the appropriate acids. By solvates of the compounds of the general formula (I) we also mean the hydrates.

The compounds of the general formula (I), as well as their pharmaceutically acceptable derivatives can be used for the treatment of diseases where human orexin receptors play a role, and for the treatment of which orexin receptor antagonists are needed.

The orexin receptor antagonistic compounds of the general formula (I), and their pharmaceutically acceptable derivatives may be appropriate for the treatment of obesity and type-II diabetes (non-insuline dependent diabetes), furthermore for the treatment of sleeping disorders, narcolepsy, insomnia, jet-lag syndrome, for the treatment of sleeping disorders connected to neurological disorders, depression, anxiety, behavioral disorders, sexual disorders, neuropathic pain, pains connected to infections (like HIV), phantome pains, postoperative pains.

The compounds of the general formula (I), and their pharmaceutically acceptable derivatives may be used for the treatment of stroke, heart- and lung diseases.

The compounds of the general formula (I), as well as their pharmaceutically acceptable derivatives can be used for the treatment and prevention of diseases where human orexin receptor antagonists are needed for the treatment. In the course of the therapy the compounds according to the invention are used in the form of pharmaceutical composition. The pharmaceutical compositions contain the compounds of the general formula (I) or their pharmaceutically acceptable derivatives, together with pharmaceutically acceptable carriers and excipients.

The compounds of the general formula (I), and their pharmaceutically acceptable derivatives can be administered by any of the traditional routes, e.g. by oral, parentheral, sublingual, nasal, rectal, or transdermal routes.

In the case of oral administation the compounds of the general formula (I) and their pharmaceutically acceptable derivatives may be given in the form of solid or liquide formulations, as for instance sirups, suspensions, emulsions, tablets or capsules.

Liquid formulations contain the active component beside an appropriate liquid vehicle (e.g. water, ethanol, glycerine, polyethyleneglycole, oil) in the form of a solution or suspension. They may also contain colouring and smelling agents.

Tablets may contain the usual additives, e.g. magnesium stearate, starch, lactose, sucrose and cellulose.

Hard and soft gelatine capsules can be prepared by the standard operations.

Parenteral formulations contain the active ingredient in the form of a solution or suspension, prepared with a sterile aqueous carrier or with an appropriate oil, as for instance polyethylene glycol, polyvinylpylpyrrolidone, sesame oil or lecitine.

For nasal application aerosols, drops, gels or powders can be applied. Aerosols contain the active ingredient in the form of an aqueous or non-aqueous solution or suspension, in a closed container, in single or multiple doses.

For rectal application suppositories may be used which contain the usual excipients (e.g. cacao-butter or coconut-butter).

For transdermal application ointments, gels or dermal paches may be used.

The doses of the compounds of the general formula (I) and their pharmaceutically acceptable derivatives used for the treatment or prevention of the above diseases depend on the nature of the disease. In case of adult patients a daily dosage of about 1 mg to 1000 mg, especially about 20 mg to about 700 mg many be applicable.

In the above dose regimens the compounds of the general formula (I) are not expected to cause toxic side effects.

CHEMICAL EXAMPLES

Example 1

Preparation of the Compounds of the General Formula (I)

2-(3-Phenyl-5-chloro-1-methyl-1H-pyrazol-4-ylmethylsulphanyl)-N-quinolin-3-ylbenzamide (I)
Ar=Ph, $R^1$=Me, $R^2$=3-quinolinyl, $R^3$H, $R^5$=Cl,
X=S, Y=CH$_2$, A=o-phenylene a) (3-Phenyl-5-chloro-1-methyl-1H-pyrazol-4-yl)methanol (V) Ar=Ph, $R^1$=Me, $R^5$=Cl To the solution made of 3-phenyl-5-chloro-1-methyl-1H-pyrazol-4-carbaldehyde (2.20 g, 0.01 mol) and 20 ml of ethanol sodium borohydride (1.89 g, 0.05 mol). is added at room temperature and the mixture is stirred for 3 hours. To the reaction mixture 100 ml of water is added, neutralized with 10% hydrochloric acid, extracted with dichloromethane (3×40 ml), dried over sodium sulphate, evaporated in vacuum; the residue is treated with diisopropyl ether (10 ml) and the white crystalline material is filtrered off. 1.76 g (79%) white crystals are obtained, mp.: 125-126° C.

NMR, $\delta_H$ (200 MHz, DMSO-$d_6$): 3.85 (s, 3H, 1-CH$_3$), 4.36 (d, 2H, J=4.8 Hz, CH$_2$OH), 5.15 (t, 1H, 1=4.8 Hz, CH$_2$OH), 7.36-7.48 (m, 3H), 7.79-7.84 (m, 2H).

b) 3-Phenyl-5-chloro-4-chloromethyl-1-n-ethyl-1H-pyrazole (VI)

Ar=Ph, $R^1$=Me, $R^5$=Cl

The mixture of (3-phenyl-5-chloro-1-methyl-1H-pyrazol-4-yl)methanol (1.11 g, 0.005 mol), thionylchloride (0.51 ml, 0.007 mol) and chloroform (15 ml) is heated under reflux conditions for 1.5 hours. The solvent is removed in vacuum. 1.11 g (92%) of light-drab-coloured solid material is obtained.

NMR, $\delta_H$ (200 MHz, DMSO-$d_6$): 3.88 (s, 3H, 1-CH$_3$), 4.74 (s, 2H, CH$_2$Cl), 7.38-7.54 (m, 3H), 7.66-7.73 (m, 2H).

c) 2-(3-Phenyl-5-chloro-1-methyl-1H-pyrazol-4-ylmethylsulphanyl)benzoic acid (II) Ar=Ph, $R^1$=Me, $R^5$=Cl, X=S, Y=CH$_2$, A=o-phenylene To the solution made of 2-mercaptobenzoic acid (1.54 g, 0.01 mol), dry potassium carbonate (1.66 g, 0.012 mol) and water (15 ml), the solution of 3-phenyl-5-chloro-4-chloromethyl-1-methyl-1H-pyrazole (2.41 g, 0.01 mol) in ethanol (45 ml) is added. The reaction mixture is stirred and heated under reflux conditions for 2 hours and evaporated in vacuum. To the solid white residue water (100 ml) is added and the mixture is acidified to pH=2 with 10% hydrochloric acid. The white crystalline material is filtered off, washed with water (2×25 ml) to obtain 3.56 g (99%) of the title acid, m.p.: 192-193° C. After recrystallisation from ethanol (130 ml) m.p.: 195-196° C.

NMR, $\delta_H$ (400 MHz, DMSO-$d_6$): 3.88 (s, 3H, 1-CH$_3$), 4.10 (s, 2H, CH$_2$S), 7.25 (m, 1H), 7.38 (m, 1H), 7.44 (m, 2H), 7.51 (m, 2H), 7.71 (m, 2H), 7.92 (m, 1H), 11.2 (broad s., 1H, COOH).

d) 2-(3-Phenyl-5-chloro-1-methyl-1H-pyrazol-4-ylmethylsulphanyl)benzoyl chloride The mixture of 2-(3-Phenyl-5-chloro-1-methyl-1H-pyrazol-4-ylmethylsulphanyl)benzoic acid (1.79 g, 0.005 mol) and thionylchloride (7 ml) is stirred and heated under reflux conditions for 1 hour. The resulting yellow-coloured solution is cooled to room temperature, diisopropyl ether (50 ml) is added to it, the mixture is stirred for 10 minutes, the precipitated white crystals are filtered off, washed with diisopropyl ether (15 ml). 1.59 g (84%) of the title acid chloride is obtained, m.p.: 182-183° C.

e) 2-(3-Phenyl-5-chloro-1-methyl-1H-pyrazol-4-ylmethylsulphanyl)-N-quinolin-3-ylbenzamide (I) Ar=Ph, $R^1$=Me, $R^2$=3-quinolinyl, $R^3$=H, $R^5$=Cl, X=S, Y=CH$_2$ Method A (FIG. 4)

The mixture of 2-(3-Phenyl-5-chloro-1-methyl-1H-pyrazol-4-ylmethylsulphanyl)benzoyl chloride (0.60 g, 0.0016 mol), 3-aminoquinoline (0.12 g, 0.0016 mol), triethylamine (0.17 g, 0.00175 mol) and dichloromethane (25 ml) is stirred and heated under reflux conditions for 3 hours. The resulting yellow-coloured solution is extracted with water (3×25 ml), dried over sodium sulphate, evaporated in vacuum, the residue is chromatographed on silicagel using CHCl$_3$/MeOH 100/1 mixture as eluent. 0.13 g (17%) of light-yellow-coloured 2-(3-Phenyl-5-chloro-1-methyl-1H-pyrazol-4-ylmethylsulphanyl)-N-quinolin-3-ylbenzamide hemihydrate is obtained. M.p.: 84-85° C.

NMR, $\delta_H$ (400 MHz, DMSO-$d_6$): 3.82 (s, 3H, 1-CH$_3$), 4.17 (s, 2H, CH$_2$S), 7.32 (m, 1H), 7.38 (m, 3H), 7.51 (m, 1H), 7.58 (m, 2H), 7.64 (m, 4H), 7.96 (m, 2H), 8.84 (s, 1H), 9.01 (s, 1H), 10.86 (s, 1H).

Example 2

2-(3-Phenyl-5-chloro-1-methyl-1H-pyrazol-4-ylmethylsulphanyl)-N-naphthalen-2-ilbenzamide (I)
Ar=Ph, $R^1$=Me, $R^2$=2-napthyl, $R^3$=H, $R^5$=Cl,
X=S, Y=CH$_2$, A=o-phenylene group Method B (FIG. 1)

The mixture of 2-(3-Phenyl-5-chloro-1-methyl-1H-pyrazol-4-ylmethylsulphanyl)benzoic acid (0.36 g, 0.001 mol), 2-aminonaplithalene (0.16 g, 0.00112 mol), 1-ethyl-3-(3'-dimethylaminopropyl)carbodiimide hydrochloride EDC) (0.22 g, 0.00114 mol), 1-hydroxybenzotriazole (HOBT) (0.014 g, 0.0001 mol) and N,N-dimethylformamide (3 ml) is stirred at room temperature for 18 hours. To the reaction mixture water is added, extracted with ethyl acetate, dried over sodium sulphate, evaporated in vacuum, the residue is chromatographed on silicagel using n-heptane/ethyl acetate 7/1-3/1 mixture as eluent. The product is crystallized in diisopropyl ether to obtain 0.21 g (43%) of the title amide, m.p.: 76° C.

According to the above methods were prepared the compounds of Examples 3-39, shown in Tables 1 and 2.

TABLE 1

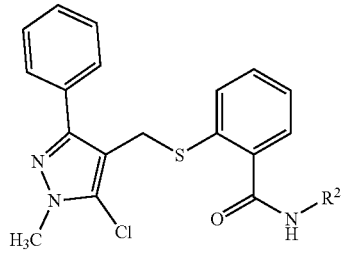

Compounds of the general formula (I),
wherein Ar = phenyl, R¹ = CH₃, R³ = H, R⁵ = Cl, X = S,
Y = —CH₂—, A = o-phenylene and R² is as given below

| Examples | Method | R² | Mp (° C.) |
|---|---|---|---|
| Example 1. | A | 3-methylquinoline | 84-85 |
| Example 2. | B | 2-methylnaphthalene | 76 |
| Example 3. | A | tolyl | 58-60 |
| Example 4. | B | N-(cyclopropylmethyl)-2-methoxy-5-methylbenzamide | 183 |
| Example 5. | B | 4-(methylthio)tolyl | 110 |
| Example 6. | A | phenethyl | 57-58 |
| Example 7. | A | 3-phenylpropyl | 101-102 |
| Example 8. | A | 4-methylquinoline | 78-80 |
| Example 9. | B | 2,4-dimethyl-1,5-naphthyridine | 145 |

TABLE 1-continued
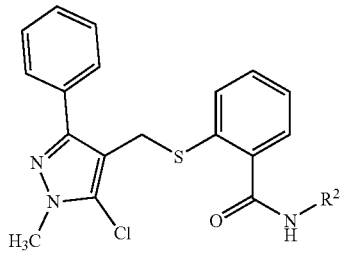
Compounds of the general formula (I),
wherein Ar = phenyl, $R^1$ = $CH_3$, $R^3$ = H, $R^5$ = Cl, X = S,
Y = —$CH_2$—, A = o-phenylene and $R^2$ is as given below
| Examples | Method | $R^2$ | Mp (° C.) |
|---|---|---|---|
| Example 10. | A | | 71-72 |
| Example 11. | A | | 217-218 HCl salt |
| Example 12. | B | | 69 |
| Example 13. | B | | 78-79 |
| Example 14. | B | | 193 |
| Example 15. | B | | 179 |
| Example 16. | B | | 60-61 |
| Example 17. | B | | 79 |
| Example 18. | B | | 158 |

TABLE 2

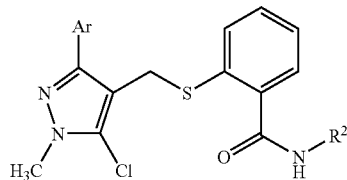

R$^1$ = CH$_3$, R$^3$ = H,
R$^5$ = Cl, X = S, Y = —CH$_2$—, A = o-phenylene

| Examples | Method of preparation | Ar | R$^2$ | Mp (° C.) |
|---|---|---|---|---|
| Example 19. | A | 4-Cl-phenyl | quinolin-3-yl | 172-173 |
| Example 20. | A | 2,5-dichloro-4-fluorophenyl | quinolin-3-yl | 86-88 |
| Example 21. | A | 3,4-dimethoxyphenyl | quinolin-3-yl | 84-87 |
| Example 22. | A | pyridin-2-yl | naphthalen-2-yl | 66-67 |
| Example 23. | A | pyridin-2-yl | quinolin-6-yl | 203-204 |
| Example 24. | A | pyridin-2-yl | quinolin-3-yl | 156-157 |
| Example 25. | A | pyridin-3-yl | naphthalen-2-yl | 83-85 |
| Example 26. | A | pyridin-3-yl | quinolin-6-yl | 236-238 |
| Example 27. | A | pyridin-3-yl | quinolin-3-yl | 184-186 |

TABLE 2-continued

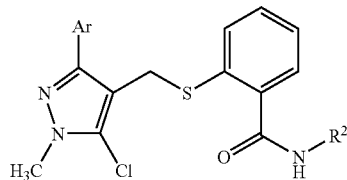

R¹ = CH₃, R³ = H,
R⁵ = Cl, X = S, Y = —CH₂—, A = o-phenylene

| Examples | Method of preparation | Ar | R² | Mp (° C.) |
|---|---|---|---|---|
| Example 28. | A | 3-pyridyl | 1-bromo-3-methylisoquinolin-yl | 172 |
| Example 29. | B | 3-pyridyl | 3-methylisoquinolin-yl | 74 (decomp.) |
| Example 30. | B | 3-pyridyl | 3-methyl-1-isobutylisoquinolin-yl | 70 |
| Example 31. | A | 3-pyridyl | 2,3,7-trimethylquinoxalin-6-yl | 105-107 |
| Example 32. | A | 3-pyridyl | 3-methylquinoxalin-2-yl | 175-176 |
| Example 33. | B | 3-pyridyl | 2,6-dimethyl-4-hydroxyquinazolin-yl | 176 |
| Example 34. | B | 3-pyridyl | 2-methyl-5-chloroquinazolin-4-yl | 75 (decomp.) |
| Example 35. | B | 3-pyridyl | 2-methyl-4-aminoquinazolin-yl | 134 (decomp.) |

TABLE 2-continued

I

R¹ = CH₃, R³ = H,
R⁵ = Cl, X = S, Y = —CH₂—, A = o-phenylene

| Examples | Method of preparation | Ar | R² | Mp (° C.) |
|---|---|---|---|---|
| Example 36. | A | 3-pyridyl | 3-methyl-N-methylbenzamide | 115 |
| Example 37. | A | 4-pyridyl | 2-naphthyl | 239-241 |
| Example 38. | A | 4-pyridyl | 3-quinolinyl | 190-191 |
| Example 39. | A | 4-pyridyl | 6-quinolinyl | 210 |

Example 40

2-(5-Chloro-1-methyl-3-pyrazin-2-yl-1M-pyrazol-4-ylmethylsulphanyl)-N-quinolin-3-ylbenzamide (I) Ar=Pyrazin-2-yl, R¹=Me, R²=3-quinolinyl, R³=H, R⁵=Cl, X=S, Y=—CH₂—, A=o-phenylene Method C (FIG. 1)

2-(5-Chloro-1-methyl-3-pyrazin-2-yl-1H-pyrazol-4-ylmethylsulphanyl)-benzoic acid (0.81 g, 0.00224 mol) is dissolved in tetrahydrofuran (35 ml) and to the solution are added: after 5 minutes of stirring 3-aminoquinoline (0.35 g, 0.00246 mol), after 5 minutes of stirring N-methylmorpholine (0.25 g, 0.00246 mol) and after 2 minutes of stirring 4-(4,6-dimethoxy-1,3,5-triazin-2-yl)-4-methylmorpholinium chloride (0.68 g, 0.00246 mol). The reaction mixture is stirred at room temperature for 2 hours, heated at reflux temperature for 1 hour. The solvent is removed in vacuum, to the reaction mixture water (100 ml) is added, extracted with dichloromethane (3×50 ml), washed with water (3×50 ml), dried over sodium sulphate and evaporated in vacuum. The residue is chromatographed on silicagel using n-hexane/ethyl acetate 10015-100/200 mixture as eluent. 0.44 (40%) of white title amide is obtained in the form of its hemihydrate, m.p: 67-69° C.

Example 41

2-(5-Chloro-1-methyl-3-pyridin-4-yl-1H-pyrazol-4-ylmethylsulphanyl)-N-(1-methylisoquinolin-3-yl)benzamide (I) Ar=Pyridin-3-yl, R¹=Me, R²=1-methyl-3-isoquinolinyl, R³=H, R⁵=Cl, X=S, Y=—CH₂—, A=o-phenylene Method E (FIG. 2)

The mixture of 3-(5-Chloro-4-chloromethyl-1-methyl-1H-pyrazol-3-yl)pyridine (0.22 g, 0.9 mmol), 2-mercapto-N-(1-methylisoquinolin-3-yl)benzamide (0.2 g, 0.7 mmol), dry potassium carbonate (0.124 g, 0.9 mmol) and N)N-dimethylformamide (10 ml) is stirred at room temperature for 17 hours. The reaction mixture is poured onto ice-water mixture, the precipitated material is filtered off, washed with water and chromatographed on silicagel using CH₂Cl₂/MeOH 99/1 mixture as eluent. 0.04 g (11%) of the title amide is obtained, m.p. 112° C.

In a similar manner is obtained the compound of Example 42, shown in Table 3.

TABLE 3

$R^1 = CH_3, R^3 = H,$
$R^5 = Cl, X = S, Y = —CH_2—, A = o\text{-phenylene}$

| Example | Method of preparation | Ar | $R^2$ | Mp (° C.) |
|---|---|---|---|---|
| Example 40. | C | pyrazinyl | 3-quinolinyl (methyl) | 67-69 |
| Example 41. | E | 4-methylpyridinyl | 3-methylisoquinolinyl | 112 |
| Example 42. | E | 4-methylpyridinyl | 1-isobutylisoquinolin-3-yl | 85 (decomp.) |

The compounds of Examples 43-46 and 49-51 were prepared according to method B of Example 2, the compound of Example 53 according to method E of Example 41.

Example 47

2-[3-Phenyl-1-(2-hydroxyethyl)-5-chloro-1H-pyrazol-4-ylmethylsulphanyl]-N-quinolin-3-ylbenzamide
(I) Ar=Phenyl, $R^1$═CH$_2$CH$_2$OH, $R^2$═3-quinolinyl,
$R^3$═H, $R^5$═Cl, X═S, Y═—CH$_2$—

To the solution of ethyl {3-phenyl-5-chloro-4-[2-(quinolin-3-ylcarbamoyl)phenylsulphanylmethyl]-1H-pyrazol-1-yl}acetate (0.34 g, 0.6 mmol) in ethanol (70 ml), sodium borohydride (0.048 g, 1.3 mmol) is added, the mixture is stirred at room temperature for 40 hours, ice-water is added and the mixture is extracted with ethyl acetate, the extract is evaporated in vacuum, the residue is chromatographed on silicagel using CH$_2$Cl$_2$/MeOH 99/1 mixture as eluent. 0.068 g (22%) of the title amide is obtained, m.p.: 95° C.

Example 48

{3-Phenyl-5-chloro-4-[2-(quinolin-3-ylcarbamoyl)phenylsulphanylmethyl]-1H-pyrazol-1-yl}acetic acid
(I) Ar Phenyl, $R^1$═CH$_2$COOH, $R^2$═3-quinolinyl,
$R^3$═H, $R^7$═Cl, X═S, Y═—CH$_2$—

Lithium hydroxide (0.045 g, 1.07 mmol) is added to the solution of ethyl {3-phenyl-5-chloro-4-[2-(quinolin-3-ylcarbamoyl)phenylsulphanylmethyl]-1H-pyrazol-1-yl}acetate (0.235 g, 0.42 mmol) in ethanol (25 ml), The reaction mixture is stirred at 40° C. for 2 hours; the solvent is removed in vacuum. To the residue water is added and the mixture is acidified to pH=4 with acetic acid. The precipitated crystalline material is filtered off, extracted with CH$_2$Cl$_2$/MeOH mixture. The filtrate is evaporated in vacuum to obtain 0.12 g (53%) of the title compound, m.p., 145° C.

Example 53

2-[3-Phenyl-5-chloro-1-(2-propylaminoethyl)-1H-pyrazol-4-ylmethylsulphanyl]-N-quinolin-3-ylbenzamide (I) Ar=Phenyl, $R^1$=CH$_2$CH$_2$NHCH$_2$CH$_2$CH$_3$, $R^2$=3-quinolinyl, $R^3$=H, $R^5$=Cl, X=S, Y=—CH$_2$—

Tosylchloride (0.067 d, 0.36 mmol) is added to the mixture of 2-[3-Phenyl-1-(2-hydroxyethyl)-5-chloro-1H-pyrazol-4-ylmethylsulphanyl]-N-quinolin-3-ylbenzamide (0,152 g, 0.29 mmol), pyridine (0.029 ml, 0.36 mmol) and dichloromethane (50 ml). The reaction mixture is stirred for 18 hours; the solvent is removed in vacuum. To the residue propyl amine (0.5 ml) is added and the mixture is heated in a closed tube at 40° C. for 5 hours, then evaporated.

The residue is chromatographed on silicagel using CH$_2$C$_2$Cl$_2$/MeOH 98/2 mixture as eluent. 0.05 g (31%) of the title amide is obtained, m.p.: 70° C.

The compounds prepared in Examples 43-53. are shown in Table 4. The compounds prepared in Examples 54-64, according to Methods A and B are demonstrated in Tables 5-7.

TABLE 4

(I)

Ar = phenyl, $R^3$ = H,
$R^5$ = Cl, X= S, Y = —CH$_2$—, A = o-phenylene group

| Example | Method of preparation | $R^1$ | Mp (° C.) |
|---|---|---|---|
| Example 43. | B | Et | 133 |
| Example 44. | B | n-Pr | 162 |
| Example 45. | B | n-Bu | 147 |
| Example 46. | B | CH$_2$COOEt | 160 |
| Example 47. | Reduction | CH$_2$CH$_2$OH | 95 |
| Example 48. | Hydrolysis | CH$_2$COOH | 145 |
| Example 49. | B | CH$_2$CONH-nPr | 102 |
| Example 50. | B | CH$_2$CONH$_2$ | 235 (decomp.) |
| Example 51. | B | morpholine-N—COCH$_2$ | 135 |
| Example 52. | E | morpholine-N—CH$_2$CH$_2$ | 80 |
| Example 53. | Amination | CH2CH2NH-n-Pr | 70 |

TABLE 5

(I)

Ar = phenyl, $R^1$ = CH$_3$,
$R^2$ = 3-quinolinyl, $R^3$= H, X = S, Y = —CH$_2$—, A = o-phenylene

| Example | Method of preparation | $R^5$ | Mp (° C.) |
|---|---|---|---|
| Example 54. | A | H | 93 |
| Example 55. | B | Me | 142 |
| Example 56. | B | SMe | 79 |

TABLE 6

(I)

$R^1$ = CH$_3$, $R^2$ = 2-naphthyl group,
$R^3$ = H, $R^5$ = Cl, X = S, Y = —CH$_2$—

| Example | Method of preparation | A | Mp (° C.) |
|---|---|---|---|
| Example 57. | B | 3,5-dimethylphenyl | 112 |
| Example 58. | B | 4-methylphenyl | 186 |
| Example 59. | B | 2-chloro-3-methylphenyl | 173 |

TABLE 6-continued

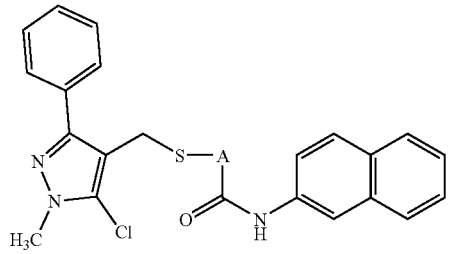

$R^1 = CH_3$, $R^2$ = 2-naphthyl group,
$R^3 = H$, $R^5 = Cl$, $X = S$, $Y = $ —$CH_2$—

| Example | Method of preparation | A | Mp (° C.) |
|---|---|---|---|
| Example 60. | B | 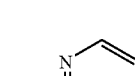 | 160-161 |

TABLE 6-continued

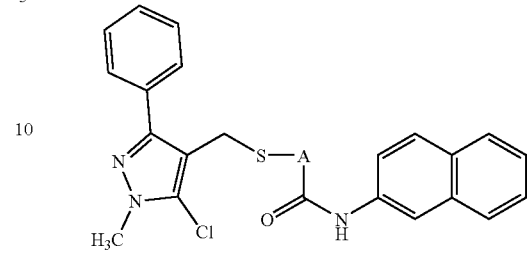

$R^1 = CH_3$, $R^2$ = 2-naphthyl group,
$R^3 = H$, $R^5 = Cl$, $X = S$, $Y = $ —$CH_2$—

| Example | Method of preparation | A | Mp (° C.) |
|---|---|---|---|
| Example 61. | B | 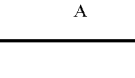 | 66-67 |

TABLE 7

I

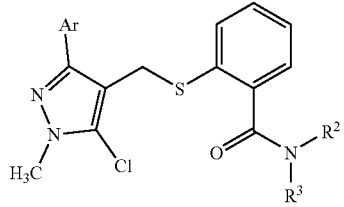

$R^1 = CH_3$, $R^5 = Cl$, $X = S$, $Y = $ —$CH_2$—, A = o-phenylene

| Example | Method of preparation | Ar | $R^2$ | $R^3$ | Mp (° C.) |
|---|---|---|---|---|---|
| Example 62. | A | phenyl | 2-naphthyl | Me | 75-77 |
| Example 63. | A | 3-pyridyl | 4-benzylpiperidinyl | | 103-106 |
| Example 64. | A | 3-pyridyl | 4-(3-trifluoromethylphenyl)-1,2,3,6-tetrahydropyridinyl | | 82-86 |

Example 65

2-(3-Phenyl-5-chloro-1-methyl-1H-pyrazol-4-yl-methoxy)-N-quinolin-3-ylbenzamide (I) Ar=Ph, $R^1$=Me, $R^2$=3-quinolinyl, $R^3$=H, $R^5$=Cl, X=O, Y=CH$_2$— a) Ethyl-2-(3-phenyl-5-chloro-1-methyl-1H-pyrazol-4-yl-methoxy)-benzoate (VII) Ar=Ph, $R^1$=Me, $R^5$=Cl, X=O The mixture of 3-phenyl-5-chloro-4-chloromethyl-1-methyl-1H-pyrazole (8.44 g, 0.035 mol), ethyl 2-hydroxybenzoate (5.82, 0.035 mol), cesium carbonate (11.40 g, 0.035 mol) and acetonitrile (200 ml) is heated under stirring for 4 hours. The reaction mixture is evaporated in vacuum, to the residue water (300 ml) is added and extracted with chloroform (3×150 ml) and evaporated in vacuum. The organic phase is washed with water (3×100 ml), dried over sodium sulphate and the solvent is removed in vacuum. The residual orange-coloured oil crystallises on addition of ethanol (10 ml). The crystals are collected, washed with ethanol (2×5 ml) to obtain 5.48 g (42%) of white crystalline ester, m.p.: 77° C.

NMR, $\delta_H$ (200 MHz, DMSO-d$_6$): 1.10 (t, J=7.1 Hz, 3H), 3.89 (s, 3H, 1-CH$_3$), 4.12 (q, J=7.1 Hz, 2H), 4.97 (s, 2H, CHO), 7.03-7.10 (m, 1H), 7.29-7.75 (m, 8H).

b) 2-(3-Phenyl-5-chloro-1-methyl-1H-pyrazol-4-yl-methoxy)benzoic acid (II) Ar=Ph, $R^1$ Me, R=Cl, X=O To the solution of ethyl-2-(3-phenyl-5-chloro-1-methyl-1H-pyrazol-4-ylmethoxy)benzoate (5.40 g, 0.0145 mol) in ethanol (35 ml) the solution of potassium hydroxide (1.63 g, 0.029 mol) in water (35 ml) is added and the reaction mixture is stirred and heated under reflux for 3 hours.

The solution is cooled down, evaporated in vacuum. The residue is dissolved in water (30 ml) and acidified to pH=3 with 10% hydrochloric acid. The white crystals are filtered off, washed with water (2×10 ml), dried and recrystallized from ethanol (35 ml). 3.43 g (69%) of white crystalline material is obtained, m.p.: 110-111° C.

c) 2-(3-Phenyl-5-chloro-1-methyl-1H-pyrazol-4-yl-methoxy)-N-quinolin-3-ylbenzamide (I) Ar=Ph, $R^1$=Me, $R^2$=3-quinolinyl, $R^3$H, $R^5$=Cl, X=O, Y=CH$_2$ Method D (FIG. 1)

2-(3-Phenyl-5-chloro-1-methyl-1H-pyrazol-4-yl-methoxy)benzoic acid (1.37 g, 0.004 mol) is dissolved in dichloromethane (50 ml), to the solution are added benzotriazol-1-yloxy-tris(pyrrolidino)phosphonium hexafluorophosphate (PyBOP) (2.08 g, 0.004 mol), 3-amino-quinoline (0.58 g, 0.004 mol) and ethyldiisopropylamine (0.90 g, 0.007 mol) are added. The solution is stirred and heated at reflux temperature for 50 hours; cooled to room temperature, extracted with water (50 ml), 10% sodium hydrogen carbonate solution (20 ml), water (3×50 ml) and evaporated in vacuum. To the residue ethanol (10 ml) is added, the resulting white crystalline material is filtered off, washed with ethanol (2×10 ml). 1.51 g (80.7%) of the title amide m.p.: 169-170° C. is obtained. After recrystallisation from ethanol m.p.: 170° C.

NMR, $\delta_H$ (400 MHz, DMSO-d$_6$): 3.84 (s, 3H, 1-CH$_3$), 5.12 (s, 2H, CH$_2$O), 7.16 (m, 1H), 7.29-7.34 (m, 3H), 7.41 (m, 1H), 7.56 (m, 2H), 7.63-7.71 (m, 4H), 7.88-7.94 (m, 2H), 8.73 (s, 2H), 10.62 (s, 1H).

The compounds of Examples 66-73. have been prepared according to method A, B, C or D.

Example 74

2-[3-(4-Fluorophenyl)-5-chloro-1-methyl-1H-pyrazol-4-ylmethoxy)-N-quinolin-3-ylbenzamide (I) Ar=4-F—C$_6$H$_4$, $R^1$=Me, $R^2$=3-quinolinyl, $R^3$=H, $R^5$=Cl, X=O, Y=—CH$_2$—

Method E (FIG. 2)

The mixture of 3-(4-fluorophenyl)-5-chloro-4-chloromethyl-1-methyl-1H-pyrazole (0.39 g, 0.0015 mol), 2-hydroxy-N-(quinolin-3-yl)benzamide (0.40 g, 0.0015 mol), cesium carbonate (0.49 g 0.0015 mol) and acetone (15 ml) is stirred and heated under reflux for 6 hours. The solvent is removed in vacuum, To the residue water (25 ml) is added. The resulting white crystalline material is filtered off and washed with water (20 ml). 0.70 g (96%) of the title amide is obtained. After recrystallisation from ethanol m.p.: 199-200° C.

NMR, $\delta_H$ (400 MHz, DMSO-d$_6$): 3.84 (s, 3H, 1-CH$_3$), 5.12 (s, 2H, CH$_2$O), 7.10-7.16 (m, 3H), 7.41 (m, 1H), 7.55-7.73 (m, 6H), 7.88-7.94 (m, 2H), 8.73 (s, 2H), 10.60 (s, 1H).

The compounds of Examples 75-77. have been prepared according to method D or E.

Data of the compounds of Examples 65-77. are demonstrated in Tables 8. and 9.

TABLE 8

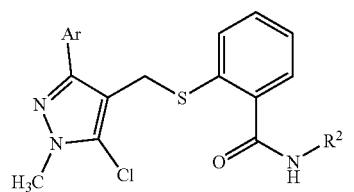

(I)

$R^1$ = CH$_3$, $R^3$ = H,
$R^5$ = Cl, X = O, Y = —CH$_2$—, A = o-phenylene

| Example | Method of preparation | Ar | $R^2$ | Mp (° C.) |
|---|---|---|---|---|
| Example 65. | D | phenyl | 3-quinolinyl | 170 |

TABLE 8-continued

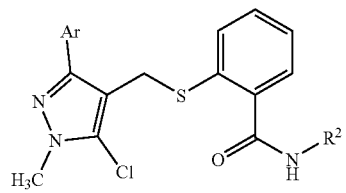

(I)

R¹ = CH₃, R³ = H,
R⁵ = Cl, X = O, Y = —CH₂—, A = o-phenylene

| Example | Method of preparation | Ar | R² | Mp (° C.) |
|---|---|---|---|---|
| Example 66. | B | phenyl | 2-naphthyl | 184 |
| Example 67. | D | phenyl | quinolin-2-yl | 186-187 |
| Example 68. | A | pyridin-3-yl | quinolin-3-yl | 179-180 |
| Example 69. | A | pyridin-4-yl | quinolin-3-yl | 177-178 |
| Example 70. | A | pyridin-2-yl | quinolin-3-yl | 159-160 |
| Example 71. | C | pyrazin-2-yl | quinolin-3-yl | 133-134 |
| Example 72. | C | 4-chlorophenyl | quinolin-3-yl | 212 |
| Example 73. | D | 3,4-dichlorophenyl | quinolin-3-yl | 138 (EtOH) |
| Example 74. | E | 4-fluorophenyl | quinolin-3-yl | 199-200 (EtOH) |
| Example 75. | D | 3-(trifluoromethyl)phenyl | quinolin-3-yl | 133 (EtOH) |

TABLE 9

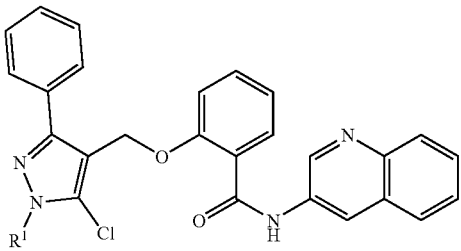

Ar = phenyl, R³ = H,
R⁵ = Cl, X = O, Y = —CH₂—, A = o-phenylene

| Example | Method of preparation | R¹ | Mp (° C.) |
|---|---|---|---|
| Example 76. | B | (benzyl group) | 153 (EtOH) |
| Example 77. | D | (4-fluorobenzyl group) | 193 (EtOH) |

The compounds of Examples 78-81 have been prepared according to method B, their data are demonstrated in Table 10.

TABLE 10

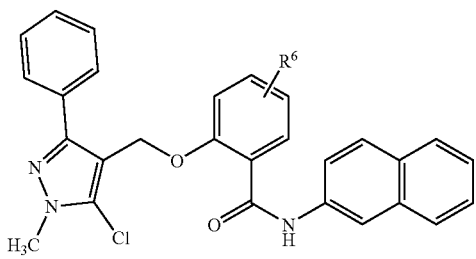

Ar = phenyl, R¹ = CH₃,
R³ = H, R⁵ = Cl, X = O, Y = —CH₂—, R² = 2-naphthyl

| Example | Method of preparation | R⁶ | Mp (° C.) |
|---|---|---|---|
| Example 78. | B | 4-F | 142 |
| Example 79. | B | 5-Cl | 164 |
| Example 80. | B | 4-MeO | 148 |
| Example 81. | B | 5-MeO | 150 |

Example 82

2-(3-Phenyl-5-chloro-1-methyl-1H-pyrazol-4-yl-methanesulphinyl)-N-naphthalen-2-ylbenzamide (1) Ar=Phenyl, R¹=Me, R²=2-naphthyl, R³=H, R⁵=Cl, X=S=O, Y=—CH₂—, A=o-phenylene 3-Chloroperbenzoic acid is added at 5° C. to the solution of 2-(3-phenyl-5-chloro-1-methyl-1H-pyrazol-4-ylmethylsulphanyl)-N-naphthalen-2-ylbenzamide (0.226 g, 0.47 mmol) in dichloromethane (20 ml). The reaction mixture is stirred at room temperature for 2 hours, diluted with ether, washed with 10% sodium hydrogencarbonate solution and evaporated in vacuum. To the residue diisopropyl ether is added, the crystals are filtered off. 0.12 (51%) of the title compound is obtained, m.p.: 195° C.

Example 83

2-[2-(3-Phenyl-5-chloro-1-methyl-1H-pyrazol-4-yl) vinyl]-N-quinolin-3-ylbenzamide (I) Ar=Phenyl, R¹=Me, R²=3-quinolinyl, R³H, R⁵=Cl, X=CH=, Y=CH=, A=o-phenylene a) (3-Phenyl-5-chloro-1-methyl-1H-pyrazol-4-ylmethyl) triphenylphosphonium chloride (X)

The mixture of 3-phenyl-5-chloro-4-chloromethyl-1-methyl-1H-pyrazol (3.63 g, 0.015 mol), triphenylphosphine (3.93 g, 0.015 mol) and toluene (75 ml) is stirred and heated under reflux for 24 hours. After cooling the resulted crystalline material is filtered off, washed with diisopropyl ether (2×15 ml) and dried. 5.36 g (71%) phosphonium salt is obtained. M.p.: >265° C.

b) Ethyl 2-[2-(3-Phenyl-5-chloro-1-methyl-1H-pyrazol-4-yl)vinyl]benzoate (VIIa)

(3-Phenyl-5-chloro-1-methyl-1H-pyrazol-4-ylmethyl) triphenylphosphonium chloride (7.86 g, 0.0156 mol) is dissolved in N,N-dimethylformamide (60 ml) and under nitrogen atmosphere 60% sodium hydride (1.25 g, 0.0312 mol), then the solution of ethyl 2-formylbenzoate (2.78 ,g 0.0156 mol) in N,N-dimethylformamide (20 ml) are added to it. The reaction mixture is stirred at room temperature for 3 hours, poured onto ice-water (150 ml), neutralized with 10% hydrochloric acid, extracted with ethyl acetate (3×150 ml), washed with water (2×100 ml), dried over sodium sulphate and evaporated. 9.81 g crude product is obtained, containing triphenylphosphine oxide as impurity beside the ester, The product is hydrolyzed into the acid without previous purification.

c) 2-[2-(3-Phenyl-5-chloro-1-methyl-1H-pyrazol-4-yl)vinyl]benzoic acid (IIa)

To the mixture of ethyl 2-[2-(3-phenyl-5-chloro-1-methyl-1H-pyrazol-4-yl)vinyl]benzoate (9.81 g, contaminated with triphenylphosphine oxide) in ethanol (30 ml) the solution of potassium hydroxide (1.75 g, 0.0312 mol) in water (30 ml) is added. The reaction mixture is stirred and heated under reflux for 2 hours, evaporated in vacuum. To the residue water (30 ml) is added and the mixture is extracted with dichlorometlhane (30 ml). To the aqueous phase 10% hydrochloric acid is added until pH=3, extracted with dichloromethane (3×35 ml), dried over sodium sulphate and evaporated. The residue is crystallized from diisopropyl ether (30 ml). 2.40 g (45%) off-white crystals are obtained, m.p.: 161-163° C. after recrystallisation from ethanol (E-isomer).

NMR, $\delta_H$ (400 MHz, DMSO-d₆): 3.90 (s, 3H, 1-CH₃), 6.87 (d, J=16.6 Hz, 1H), 7.36-7.60 (m, 7H), 7.70 (m, 1H), 7.81 (m, 1H), 7.90 (d, J=16.6 Hz, 1H), 13.0 (broad s, 1H).

d) 2-[2-(3-Phenyl-5-chloro-1-methyl-1H-pyrazol-yl)vinyl]-N-quinolin-3-ylbenzamide (I)

Method A (FIG. 1)

The mixture of 2-[2-(3-Phenyl-5-chloro-1-methyl-1H-pyrazol-4-yl)vinyl]benzoic acid (E-isomer, 1.01 g, 0.003 mol) and thionyl chloride (7 ml) is stirred and heated under reflux for 2 hours. The solution is evaporated in vacuum, to the residue 3-aminoquinoline (0.43 g, 0.003 mol), triethylamine (0.607 g, 0.006 mol) and dichloromethane (30 ml) are added. The solution is stirred and heated under reflux for 5 hours, extracted consecutively with water (50 ml), 10% sodium hydrogencarbonate solution (50 ml) and water (2×50 ml), dried over sodium sulphate and evaporated. The residue is chromatographed on silicagel using $CHCl_3$/MeOH 100/1 mixture as eluent. 0.35 g (25%) orange-coloured crystalline amide is obtained, m.p.: 197-201° C. E-isomer)

Example 84

2-[2-(3-Phenyl-5-chloro-1-methyl-1H-pyrazol-4-yl)ethyl]-N-quinolin-3-ylbenzamide (I) Ar=Phenyl, $R^1$=Me, $R^2$=3-quinolinyl, $R^3$=H, $R^5$=Cl, X=$CH_2$, Y=$CH_2$, A=o-phenylene;

a) 2-[2-(3-Phenyl-5-chloro-1-methyl-1H-pyrazol-4-yl)ethyl]benzoic acid (IIb)

2-[2-(3-Phenyl-5-chloro-1-methyl-1H-pyrazol-4-yl)vinyl]benzoic acid (0.70 g, 0.00207 mol) dissolved in 96% ethanol (50 ml) is hydrogenated in the presence of 10% Pd/C catalyst (0.15 g) at 35° C. under 1 bar pressure. The catalyst is filtered off, the solvent is removed in vacuum. 0.70 g acid is obatined in the form of pale-yellow oil.

b) 2-[2-(3-Phenyl-5-chloro-1-methyl-1H-pyrazol-4-yl)ethyl]-N-quinolin-3-ylbenzamide (I)

Method C (FIG. 1)

2-[2-(3-Phenyl-5-chloro-1-methyl-1H-pyrazol-4-yl)ethyl]benzoic acid (IIc, 0.70 g, 0.002 mol) is dissolved in tetrahydrofuran (35 ml), to the solution are added: 3-aminoquinoline (0.29 g, 0.002 mol), then after 3 minutes of stirring N-methylmorpholine (0.2 g, 0.002 mol), then after 5 minutes of stirring 4-(4,6-dimethoxy-1,3,5-triazin-2-yl)-4-methylmorpholinium chloride (0.55 g, 0.002 mol). The white suspension is stirred at room temperature for 2.5 hours, then heated at reflux temperature for 3 hours and evaporated in vacuum. To the residue water (100 ml) and chloroform (100 ml) are added, the organic phase is washed with 10% sodium carbonate solution (75 ml), water (75 ml), dried over sodium sulphate and evaporated. The residual yellow oil (0.95 g) is chromatographed on silicagel using n-hexane/ethyl acetate 100/10-100/140 solvent mixture as eluent. 0.38 g (41%) of white crystalline amide is obtained, m.p.: 139-140° C.

Example 85

2-[2-(5-Chloro-1-methyl-3-pyridin-3-yl-1H-pyrazol-4-yl) ethyl]-N-quinolin-3-ylbenzamide (I)

Ar=3-pyridyl, $R^1$=Me, $R^2$=3-quinolinyl, $R^3$=H, $R^5$=Cl, X=$CH_2$, Y=$CH_2$, A=o-phenylene a) (5-Chloro-1-methyl-3-pyridin-3-yl-1H-pyrazol-4-ylmethyl) triphenylphosphonium chloride hydrochloride (X)

The mixture of 3-(5-chloro-4-chloromethyl-1-methyl-1H-pyrazol-3-yl)pyridine hydrochloride (2.78 g, 0.01 g), tiphenylphosphine (2.75 g, 0.0105 mol) and xylene (50 ml) is stirred and heated under reflux conditions for 18 hours. After cooling the precipitated crystals are filtered off, washed with diisopropyl ether (2×10 ml) and dried. 4.0 g (68.2%) of white phosphonium salt is obtained.

b) Ethyl 2-[2-(5-chloro-1-methyl-3-pyridin-3-yl-1H-pyrazol-4-yl)vinyl]-benzoate (VIIa)

(5-Chloro-1-methyl-3-pyridin-3-yl-1H-pyrazol-4-ylmethyl)triphenyl phosphonium chloride hydrochloride (X, 5.68 g, 0.0105 mol) is dissolved in N,N-dimethylformamide (60 ml) and under nitrogen atmosphere 60% sodium hydride (1.04 g, 0.026 mol) is added to it. To the resulting suspension the solution of ethyl 2-formylbenzoate (1.87 g, 0.0105 mol) in N,N-dimethylformamide (10 ml) is added, the mixture is stirred at room temperature for 3 hours, then poured onto ice-water (150 ml). The precipitated crystals are filtered off and washed with water (25 ml). 1.59 g (40.7%) of the title ester is obtained. After recrystallisation from ethanol m.p.: 102-103° C. (E-izomer).

NMR, $\delta_H$ (400 MHz, DMSO-$d_6$). 1.26 (t, J=7.08 Hz, 3H, COOCH$_2$CH$_3$), 3.92 (s, 3H, 1-CH$_3$), 4.25 (q, J=7.08 Hz, 2H, COOCH$_2$CH$_3$), 6.91 (d, J=16.5 Hz, 1H), 7.38-7.40 (m, 1H), 7.49-7.56 (m, 2H), 7.73-7.79 (m, 3H), 7.97-7.99 (m, 1H) 8.60-8.62 (m, 1H), 8.78 (d, J=1.4 Hz, 1H)

c) 2-[2-(5-chloro-1-methyl-3-pyridin-3-yl-1H-pyrazol-4-yl) vinyl]-benzoic acid (IIa)

To the mixture of ethyl 2-[2-(5-chloro-1-methyl-3-pyridin-3-yl-1H-pyrazol-4-yl)vinyl]-benzoate (VIIb, 0.94 g, 0.0025 mol) and ethanol (10 ml) the solution of potassium hydroxide (0.28 g, 0.005 mol) in water (10 ml) is added. The reaction mixture is stirred and heated under reflux for 2 hours, evaporated in vacuum. To the residue water (15 ml) is added and the mixture is acidified to pH=3 with 10% hydrochloric acid solution. The resulting crystals are filtered off, washed with water (2×10 ml). 0.66 g (77.6%) of the title acid is obtained, m.p.: 183-185° C. E-isomer).

d) 2-[2-(5-Chloro-1-methyl-3-pyridin-3-yl-1H-pyrazol-4-yl) ethyl]benzoic acid (IIb)

2-[2-(5-Chloro-1-methyl-3-pyridin-3-yl-1H-pyrazol-4-yl)vinyl]benzoic acid (IIb, 0.66 g, 0.00194 mol) is hydrogenated according to the method described in Example 84a). 0.50 g of the title acid is obtained in the form of pale-yellow oil. $R_f$ 0.45 ($CHCl_3$MeOH 9/1).

e) 2-[2-(5-Chloro-1-methyl-3-pyridin-3-yl-1H-pyrazol-4-yl) ethyl]-N-quinolin-3-ylbenzamide (I)

Method C (FIG. 1)

Starting from 2-[2-(5-Chloro-1-methyl-3-pyridin-3-yl-1H-pyrazol-4-yl)ethyl]benzoic acid (IIc, 0.97 g, 0.0028 mol) and 3-aminoquinoline (0.40 g, 0.0028 mol) according to the method described in Example 84b) 0.25 (18.4%) of the white crystalline title amide is obtained, m.p.: 142-144° C.

Example 86

2-[(3-Phenyl-5-chloro-1-methyl-1H-pyrazol-4-ylmethyl)amino]-N-naphthalen-2-ylbenzamide (I)
Ar=Phenyl, $R^1$=Me, $R^2$=2-naphthyl, $R^3$=H, $R^5$=Cl, X=NH, Y=$CH_2$, A=o-phenylene;

a) Ethyl-2-[(3-phenyl-5-chloro-1-methyl-1H-pyrazol-4-ylmethyl)amino]benzoate (VII)

To the solution of 3-phenyl-5-chloro-4-chloromethyl-1-methyl-1H-pyrazol (2.03 g, 0.00844 mol) in ethanol (40 ml) the mixture of ethyl 2-aminobenzoate (1.39 g, 0.00844 mol), dry potassium carbonate (1.38 g, 0.01 mol) and water (10 ml) is added and the reaction mixture is stirred and heated under reflux for 2 hours. The solvent is removed in vacuum, to the residue water (50 ml) is added the mixture is neutralized with 10% hydrochloric acid solution, extracted with ethyl acetate (2×50 ml); the organic phase is washed with water (50 ml), dried over sodium sulphate and evaporated in vacuum. The residue is recrystallized from ethanol. 0.5 g (16%) of white crystalline ester is obtained, m.p.: 123° C.

b) 2-[(3-Phenyl-5-chloro-1-methyl-1H-pyrazol-4-ylmethyl) amino]benzoic acid (II)

Ethyl-2-[(3-phenyl-5-chloro-1-methyl-1H-pyrazol-4-ylmethyl)amino]benzoate (VIIa, 1.02 g, 0.00276 mol) is hydrolyzed according to the method described in Example 65b). 0.80 g (85%) white crystalline acid is obtained. After recrystallisation from ethanol, m.p.: 192-193° C.

c) 2-[(3-Phenyl-5-chloro-1-methyl-1H-pyrazol-4-ylmethyl) amino]-N-naphthalen-2-ylbenzamide (I)

Method C (FIG. 1)

Starting from 2-[(3-phenyl-5-chloro-1-methyl-1H-pyrazol-4-ylmethyl)amino]benzoic acid (IIa, 0.96 g, 0.0028 mol) and 2-aminonaphthalene (0.44 g, 0.0031 mol) according to the method described in Example 84b) 0.30 g (23%) white crystalline amide is obtained, m.p.: 83-85° C.

Example 87

3-(3-Phenyl-5-chloro-1-methyl-1H-pyrazol-4-ylmethoxy)-N-quinolin-3-ylpropionamide (I) Ar Phenyl, $R^1$=Me, $R^2$=3-quinolinyl, $R^3$=H, $R^5$=Cl, X=O, Y=$CH_2$, A=CH—CH, 3-(3-Phenyl-5-chloro-1-methyl-1H-pyrazol-4-ylmethoxy)propionic acid (0.75 g, 0.0025 mol) is dissolved in dichloromethane (25 ml) and to the solution benzotriazol-1-yloxy-tris(pyrrrolidino)phosphonium hexafluorophosphate (PyBOP) (1.30 g, 0.0025 mol), 3-aminoquinoline (0.36 g, 0.0025 mol) and ethyl diisopropylamine (0.56 g, 0.004375 mol) are added. The solution is stirred and heated for 24 hours, cooled to room temperature, extracted consecutively with water (50 ml), 10% sodium hydrogen carbonate solution (15 ml), and water (2×50 ml), dried over sodium sulphate, evaporated in vacuum. The residue is chromatographed on silicagel using $CH_2Cl_2$/MeOH 100/1-100/10 solvent mixture as eluent. The resulting material is crystallized from diisopropyl ether (30 ml). 0.89 g (84.7%) of the title amide is obtained in the form of hemihydrate, m.p.: 156-157° C.

Example 88

5-(3-Phenyl-5-chloro-1-methyl-1H-pyrazol-4-yl) pentane carboxylic acid N-quinolin-3-ylamide (I) Ar=Phenyl, $R^1$=Me, $R^2$=3-quinolinyl, $R^3$=H, $R^5$=Cl, X=—$CH_2$—, Y=—$CH_2$—, A —$CH_2CH_2$—

From 5-(3-Phenyl-5-chloro-1-methyl-1H-pyrazol-4-yl) pentane carboxylic acid (0.88 g, 0.003 mol) and 3-aminoquinoline (0.43 g, 0.003 mol) according to the method described in Example 87., 0.73 g (54%) of pale-yellow amide containing 1.5 mol of crystal water is obtained; m.p.: 53-55° C.

Example 89

2-[(3-Phenyl-5-chloro-1-methyl-1H-pyrazol-4-ylmethyl)methylamino]-N-quinolin-3-ylbenzamide (I) Ar=Ph, $R^1$=Me, $R^2$=3-quinolinyl, $R^3$=H, $R^5$=Cl, X=NMe, Y=—$CH_2$— a) Ethyl 2-[(3-phenyl-5-chloro-1-methyl-1H-pyrazol-4-ylmethyl)methylamino]benzoate (VII) Ar=Ph, $R^1$=Me, $R^5$=Cl, X=NMe To the mixture of ethyl 2-[(3-phenyl-5-chloro-1-methyl-1H-pyrazol-4-ylmethyl)amino]benzoate (1.28 g, 3.46 mmol), paraformaldehyde (1.04 g, 34.64 mol) and acetic acid (35 ml) under stirring at 10° C. sodium cyanoborohydride (1.09 g, 17.34 mmol) is added. The reaction mixture is stirred at 25° C. for 20 hours, then poured into the mixture of 25% sodium hydroxide solution (90 ml) and ice-water (110 ml), extracted with dichloromethane (3×100 ml); the organic phase is washed with water (2×200 ml), dried over sodium sulphate and evaporated in vacuum. 1.09 g (82%) of the title ester is obtained. [M–H]$^+$384.

NMR, $\delta_H$ (200 MHz, $CDCl_3$): 1.15 (t, J=7.2 Hz, 3H), 2.64 (s, 3H, $NCH_3$), 3.83 (s, 3H, 1-$CH_3$), 4.10 (s, 2H, $CH_2NCH_3$), 4.19 (q, J=7.2 Hz, 2H), 6.82-6.92 (m, 2H), 7.16-7.33 (m, 4H), 7.55 (m, 3H).

b) 2-[(3-Phenyl-5-chloro-1-methyl-1H-pyrazol-4-ylmethyl) methylamino]benzoic acid (II) Ar=Ph, $R^1$=Me, $R^5$=Cl, X=NMe To the solution of ethyl 2-[(3-phenyl-5-chloro-1-methyl-1H-pyrazol-4-ylmethyl)methylamino]benzoate (0.99 g, 2.43 mmol) in ethanol (5 ml) the solution of potassium hydroxide (0.29 g, 5.17 mmol) in water (5 ml) is added and the reaction mixture is stirred and heated under reflux for 4 hours. The mixture is cooled and evaporated in vacuum. The residue is dissolved in water (15 ml), acidified to pH=3 with 10% hydrochloric acid, extracted with chloroform (50 ml), dried over sodium sulfate and evaporated. 0.79 g (91.8%) of the title acid is obtained. [M–H]$^+$356.

NMR, $\delta_H$ (200 MHz, $CDCl_3$); 2.63 (s, 3H, $NCH_3$), 3.79 (s, 3H, 1-$CH_3$), 4.21 (s, 2H, $CH_2NCH_3$), 7.04 (m, 1H), 7.15-7.32 (m, 7H), 8.10 (m, 1H).

c) 2-[(3-Phenyl-5-chloro-1-methyl-1H-pyrazol-4-ylmethyl) methylamino]-N-quinolin-3-ylbenzamide (I) Ar=Ph, $R^1$=Me, R-=3-quinolinyl, $R^3$H, $R^5$=Cl, X=NMe, Y=$CH_2$ Method D (FIG. 1)

2-[(3-Phenyl-5-chloro-1-methyl-1H-pyrazol-4-ylmethyl) methylamino]benzoic acid (0.79 g, 2.22 mmol) is dissolved in dichloromethane (25 ml), to this solution benzotriazol-1-yloxy-tris(pyrrolidino)phosphonium hexafluorophosphate (PyBOP) (1.555 g, 2.22 mol), 3-aminoquinoline (0.32 g, 2.22 mmol) and ethyldiisopropylamine (0.50 g, 3.89 mmol) are added. The solution is stirred and heated under reflux for 88 hours, cooled to room temperature, extracted consecutively with water (50 ml), 10% sodium hydrogencarbonate solution (25 ml) and water (3×50 ml), dried over sodium sulphate and evaporated in vacuum. To the residue ethanol (5 ml) is added, the pale-yellow crystalline material is filtered off, washed with ethanol (2×5 ml). 0.69 g (64.5%) of the title amide is obtained; m.p.: 179-180° C.

NMR, $\delta_H$ (400 MHz, DMSO-$d_6$): 2.68 (s, 3H, $NCH_3$), 3.80 (s, 3H, 1-$CH_3$), 4.27 (s, 2H, $CH_2NCH_3$), 7.13 (m, 1H), 7.18-7.22 (m, 3H), 7.37 (m, 1H), 7.44 (m, 1H), 7.57-7.65 (m, 4H), 7.82 (m, 1H), 7.89 (m, 1H), 7.95 (m, 1H), 8.63 (s, 1H), 8.66 (s, 1H), 11.71 (s, 1H).

TABLE 10/A

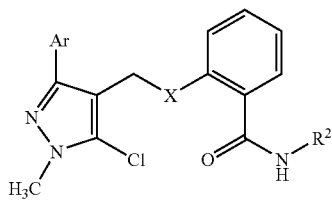

$R^1 = CH_3, R^3 = Cl, Y = -CH_2-$

| Example | Method of preparation | Ar | X | R² | Mp (° C.) |
|---|---|---|---|---|---|
| Example 90. | D | 2-chlorophenyl | O | quinolin-3-yl | 143-144 |
| Example 91. | D | 2-fluorophenyl | O | quinolin-3-yl | 125 |
| Example 92. | D | 4-pyridyl | S | 3,4-dichlorophenyl | 155-157 |
| Example 93. | D | 2-thienyl | O | quinolin-3-yl | 187-188 |
| Example 94. | D | 3-pyridyl | O | benzothiazol-2-yl | 197-198 |
| Example 95. | D | pyridazin-4-yl | NCH₃ | quinolin-3-yl | 176-177 |
| Example 96. | D | 3-pyridyl | O | 3,4-dichlorophenyl | 133-134 |
| Example 97. | D | 3-pyridyl | O | 6,7-difluoroquinolin-3-yl | 185 |

Preparation of the Intermediates

TABLE 11

The new intermediates of the general formula (IV) are prepared as described in the literature (J. Org. Chem. 1992, 57, 2127)

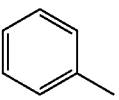

| Example | Ar | R$^1$ | R$^5$ | Mp ° C. or $^1$H—NMR [DMSO-d$_6$] or LCMS [M + H]$^+$ |
|---|---|---|---|---|
| IV-1 | 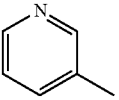 | CH$_3$ | Cl | J. Org. Chem. 1992, 57, 2127 |
| IV-2 | 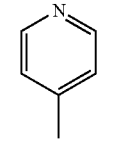 | CH$_3$ | Cl | 94° C.<br>9.83 (s, 1H, CHO), 3.94 (s, 3H, NCH$_3$) |
| IV-3 | 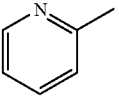 | CH$_3$ | Cl | 109-110° C.<br>9.88 (s, 1H, CHO), 3.94 (s, 3H, NCH$_3$) |
| IV-4 | 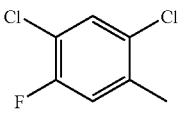 | CH$_3$ | Cl | 135-136° C.<br>10.58 (s, 1H, CHO), 3.91 (s, 3H, NCH$_3$) |
| IV-5 | 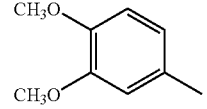 | CH$_3$ | Cl | 107-108° C.<br>9.67 (s, 1H, CHO), 3.93 (s, 3H, NCH$_3$) |
| IV-6 | 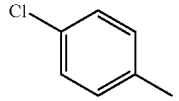 | CH$_3$ | Cl | 115-116° C.<br>9.84 (s, 1H, CHO), 3.90 (s, 3H, NCH$_3$),<br>3.80 (s, 6H, OCH$_3$) |
| IV-7 | 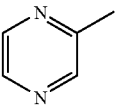 | CH$_3$ | Cl | 77-78° C.<br>9.83 (s, 1H, CHO), 3.92 (s, 3H, NCH$_3$) |
| IV-8 | 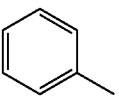 | CH$_3$ | Cl | 154-156° C.<br>10.42 (s, 1H, CHO), 3.95 (s, 3H, NCH$_3$) |
| IV-9 | 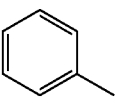 | C$_2$H$_5$ | Cl | δ (CDCl$_3$): 1.49 (t, 3H; 4.30 (q, 2H), 7.3-7.5 (m, 3H), 7.68-7.79 (m, 2H); 9.92 (s, 1H) |
| IV-10 |  | C$_3$H$_7$ | Cl | δ (CDCl$_3$): 1.17 (t, 3H); 2.11 (m, 2H); 4.34 (t, 2H); 7.55-7.68 (m, 3H; 7.85-7.97 (m, 2H); 10.07 (s, 1H) |

TABLE 11-continued

The new intermediates of the general formula (IV) are prepared as described in the literature (J. Org. Chem. 1992, 57, 2127)

IV

| Example | Ar | R¹ | R⁵ | Mp ° C. or ¹H—NMR [DMSO-d₆] or LCMS [M + H]⁺ |
|---|---|---|---|---|
| IV-11 | phenyl | $C_4H_9$ | Cl | δ (CDCl₃): 1.22 (t, 3H); 1.69 (m, 2H); 2.18 (m, 2H); 4.52 (t, 2H); 7.67-7.80 (m, 3H); 7.95-8.08 (m, 2H; 10.19 (s, 1H) |
| IV-12 | phenyl | $CH_2COOC_2H_5$ | Cl | 293.3 |
| IV-13 | phenyl | $CH_2CH_2Cl$ | Cl | 269.2 |
| IV-14 | phenyl | morpholinopropyl | Cl | δ (CDCl₃): 2.51-2.61 (m, 4H); 2.92 (t, 2H); 3.65-3.77 (m 2H); 4.38 (t, 2H); 7.41-7.53 (m, 3H); 7.71-7.83 (m, 2H); 9.98 (s, 1H) |
| IV-15 | phenyl | $CH_3$ | $CH_3$ | δ (CDCl₃): 2.51 (s, 3H); 3.80 (s, 3H; 7.29-7.42 (m, 3H); 7.49-7.61 (m, 2H); 9.88 (s 1H) |
| IV-16 | phenyl | $CH_3$ | $SCH_3$ | 233.3 |
| IV-17 | 3,4-dichlorophenyl | $CH_3$ | Cl | 90-92° C. 9.83 (s, 1H, CHO), 3.93 (s, 3H, NCH₃) |
| IV-18 | 4-fluorophenyl | $CH_3$ | Cl | 76-77° C. 9.82 (s, 1H, CHO), 3.91 (s, 3H, NCH₃) |
| IV-19 | 3-trifluoromethylphenyl | $CH_3$ | Cl | 49-51° C. 9.85 (a, 1H, CHO), 3.93 (s, 3H, NCH₃) |
| IV-20 | 2-methoxyphenyl | $CH_3$ | Cl | 97-98° C. |
| IV-21 | phenyl | H | Cl | 195-197° C. 9.83 (s, 1H, CHO) |

TABLE 11-continued

The new intermediates of the general formula (IV) are prepared as described in the literature (J. Org. Chem. 1992, 57, 2127)

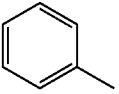

IV

| Example | Ar | R¹ | R⁵ | Mp °C. or $^1$H—NMR [DMSO-$d_6$] or LCMS [M + H]$^+$ |
|---|---|---|---|---|
| IV-22 | 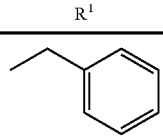 | 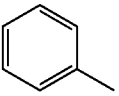 | Cl | 9.87 (s, 1H, CHO), 5,53 (s, 2H, CH$_2$Ph) |
| IV-23 | 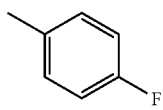 | 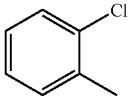 | Cl | 78-82° C. 9.96 (s, 1H, CHO) |
| IV-24 | 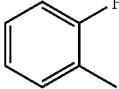 | CH$_3$ | Cl | 95-96° C. |
| IV-25 | 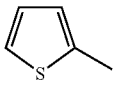 | CH$_3$ | Cl | 88-89° C. |
| IV-26 | 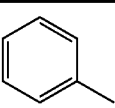 | CH$_3$ | Cl | δ (CDCl$_3$): 9.93 (s, 1H, CHO), 3.85 (s, 3H, NCH$_3$) |

TABLE 12

The new intermediates of the general formula (V) are prepared as described in Example 1a)

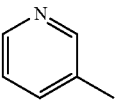

V

| Example | Ar | R¹ | R⁵ | Mp (° C.) or $^1$H-NMR [CDCl3] |
|---|---|---|---|---|
| V-1 | (phenyl) | CH$_3$ | Cl | 125-126° C. white crystals |
| V-2 | (3-pyridyl) | CH$_3$ | Cl | 189° C. white crystals |

TABLE 12-continued

The new intermediates of the general formula (V) are prepared as described in Example 1a)

| Example | Ar | R¹ | R⁵ | Mp (° C.) or ¹H-NMR [CDCl3] |
|---|---|---|---|---|
| V-3 | 4-pyridyl | CH₃ | Cl | 148-150° C. white crystals |
| V-4 | 2-pyridyl | CH₃ | Cl | 112-113° C. white crystals |
| V-5 | 2,5-dichloro-4-fluorophenyl | CH₃ | Cl | 114-116° C. white crystals |
| V-6 | 3,4-dimethoxyphenyl | CH₃ | Cl | 141-142° C. white crystals |
| V-7 | 4-chlorophenyl | CH₃ | Cl | 126-128° C. (EtOH) white crystals |
| V-8 | 2-pyrazinyl | CH₃ | Cl | 173-174° C. off-white crystals |
| V-9 | phenyl | C₂H₅ | Cl | 1.41 (t, 3H); 1.69 (t,1H); 4.12 (q, 2H); 4.62 (d, 2H); 7.41-7.58 (m, 3H); 7.70-7.82 (m, 2H) |
| V-10 | phenyl | C₃H₇ | Cl | 0.85 (t, 3H); 1.48 (t, 1H); 1.88 (m, 2H); 4.08 (t, 2H); 4.67 (d, 2H); 7.21-7.42 (m, 3H); 7.67-7.75 (m, 2H) |
| V-11 | phenyl | C₄H₉ | Cl | 0.88 (t, 3H); 1.30 (m, 2H); 1.68-1.88 (m, 3H); 4.08 (t, 2H); 4.49 (d, 2H); 7.21-7.39 (m, 3H); 7.65-7.75 (m, 2H) |
| V-12 | phenyl | CH₂COOC₂H₅ | Cl | 98° C. |

TABLE 12-continued
The new intermediates of the general formula (V) are prepared as described in Example 1a)
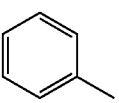
| Example | Ar | R¹ | R⁵ | Mp (° C.) or ¹H-NMR [CDCl3] |
|---|---|---|---|---|
| V-13 | 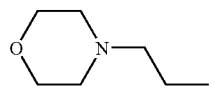 | 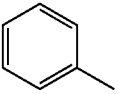 | Cl | [M + H]⁺ 322.3 |
| V-14 | 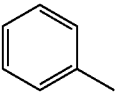 | CH₃ | CH₃ | 1.36 (t, 1H); 2.19 (s, 3H); 3.72 (s, 3H); 4.48 (d, 2H); 7.20-7.39 (m, 3H); 7.58-7.71 (m, 2H) |
| V-15 | 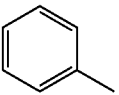 | CH₃ | SCH₃ | 1.58 (t, 1H); 2.22 (s, 3H); 3.94 (s, 3H); 4.68 (d, 2H); 7.29-7.45 (m, 3H); 7.68-7.79 (m, 2H) |
| V-16 | 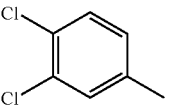 | CH₃ | H | [M + H]⁺ 189.3 |
| V-17 | 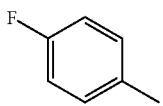 | CH₃ | Cl | 185-187° C. off-white crystals |
| V-18 | 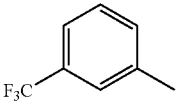 | CH₃ | Cl | 154° C. white crystals |
| V-19 | 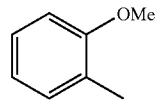 | CH₃ | Cl | 124-125° C. off-white crystals |
| V-20 | 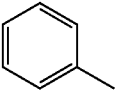 | CH₃ | Cl | 82-83° C. white crystals |
| V-21 | 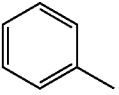 | H | Cl | 221-223° C. |
| V-22 | 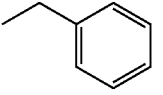 | 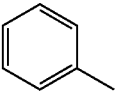 | Cl | 114-115° C. white crystals |
| V-23 | 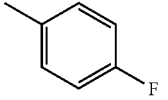 |  | Cl | 125-127° C. |

TABLE 12-continued

The new intermediates of the general formula (V) are prepared as described in Example 1a)

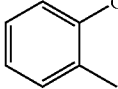
(V)

| Example | Ar | $R^1$ | $R^5$ | Mp (° C.) or $^1$H-NMR [CDCl3] |
|---|---|---|---|---|
| V-24 | 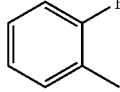 | $CH_3$ | Cl | 124-125° C. |
| V-25 | 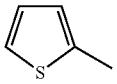 | $CH_3$ | Cl | 106-107° C. |
| V-26 | 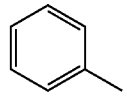 | $CH_3$ | Cl | 149-151° C. |

TABLE 13

The new intermediates of the general formula (VI) are prepared as described in Example 1b)

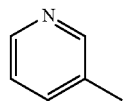
(VI)

| Example | Ar | $R^5$ | $^1$H-NMR [DMSO-$d_6$] or LCMS [M + H]$^+$ |
|---|---|---|---|
| VI-1 | 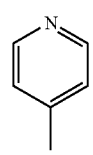 | Cl | white crystals 3.88 (s, 3H, NCH$_3$), 4.74 (s, 2H, CH$_2$Cl) |
| VI-2 | 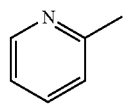 | Cl | hydrochloride 3.93 (s, 3H, NCH$_3$), 4.88 (s, 2H, CH$_2$Cl) |
| VI-3 | | Cl | hydrochloride 3.97 (s, 3H, NCH$_3$), 4.93 (s, 2H, CH$_2$Cl) |
| VI-4 | | Cl | hydrochloride 3.91 (s, 3H, NCH$_3$), 5.13 (s, 2H, CH$_2$Cl) |

TABLE 13-continued

The new intermediates of the general formula (VI) are prepared as described in Example 1b)

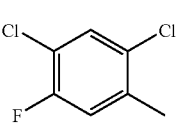
(VI)

| Example | Ar | R⁵ | ¹H-NMR [DMSO-d₆] or LCMS [M + H]⁺ |
|---|---|---|---|
| VI-5 | 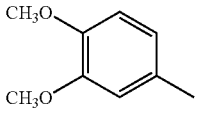 | CH₃ | Cl 3.88 (s, 3H, NCH₃), 4.54 (s, 2H, CH₂Cl) |
| VI-6 | 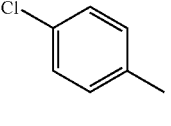 | CH₃ | Cl hydrochloride 3.80 (s, 6H, OCH₃), 3.86 (s, 3H, NCH₃), 4.73 (s, 2H, CH₂Cl) |
| VI-7 | 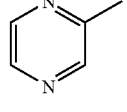 | CH₃ | Cl 3.87 (s, 3H, NCH₃), 4.74 (s, 2H, CH₂Cl) |
| VI-8 | 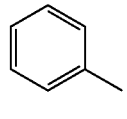 | CH₃ | Cl hydrochloride 3.94 (s, 3H, NCH₃), 5.07 (s, 2H, CH₂Cl) |
| VI-9 | 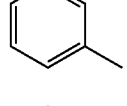 | C₂H₅ | Cl [CDCl₃] 1.28 (t, 3H); 4.09 (q, 2H); 4.44 (s, 2H); 7.13-7.67 (m, 5H) |
| VI-10 | 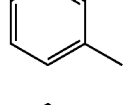 | C₃H₇ | Cl [CDCl₃] 0.89 (t, 3H); 1.82 (m, 2H); 4.12 (t, 2H); 4.56 (s, 2H); 7.27-7.42 (m, 3H); 7.60-7.70 (m, 2H) |
| VI-11 | 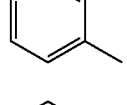 | C₄H₉ | Cl [CDCl₃] 0.89 (t, 3H); 1.31 (m, 2H); 1.80 (m, 2H); 4.09 (t, 2H); 4.52 (s, 2H); 7.25-7.45 (m, 3H); 7.62-7.71 (m, 2H) |
| VI-12 | 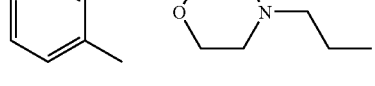 | CH₂COOC₂H₅ | Cl [CDCl₃] 1.15 (t, 3H); 4.18 (q, 2H); 4.51 (s, 2H); 4.88 (s, 2H); 7.27-7.40 (m, 3H); 7.63-7.71 (m, 2H) |
| VI-13 | 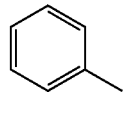 | (N-propylmorpholine) | Cl [M + H]⁺ 340,3 |
| VI-14 | 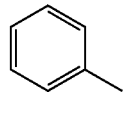 | CH₃ | CH₃ [CDCl₃] 2.48 (s, 3H); 4.27 (s, 3H); 4.51 (s, 2H); 7.49-7.60 (m, 3H), 7.78-7.91 (m 2H) |

TABLE 13-continued

The new intermediates of the general formula (VI) are prepared as described in Example 1b)

(VI)

| Example | Ar | R⁵ | ¹H-NMR [DMSO-d₆] or LCMS [M + H]⁺ |
|---|---|---|---|
| VI-15 | phenyl | CH₃ | SCH₃ [M + H]⁺ 249,2 |
| VI-16 | phenyl | CH₃ | H  3.86 (s, 3H, NCH₃), 4.82 (s, 2H, CH₂Cl), 7.92 (s, 1H, 5-H) |
| VI-17 | 4-F-phenyl | CH₃ | Cl  62-64° C. 3.88 (s, 3H, NCH₃), 4.77 (s, 2H, CH₂Cl) |
| VI-18 | 4-F-phenyl | CH₃ | Cl  73-75° C. 3.85 (s, 3H, NCH₃), 4.73 (s, 2H, CH₂Cl) |
| VI-19 | 3-CF₃-phenyl | CH₃ | Cl  42-44° C. 3.88 (s, 3H, NCH₃), 4.78 (s, 2H, CH₂Cl) |
| VI-20 | 2-OMe-phenyl | CH₃ | Cl  68-69° C. |
| VI-21 | phenyl | CH₂-phenyl | Cl  103-104° C. [CDCl₃] 4.52 (s, 2H, CH₂Cl), 5.32 (s, 2H, CH₂Ph) |
| VI-22 | phenyl | 4-F-phenyl | Cl  74-76° C. 4.83 (s, 2H, CH₂Cl) |
| VI-23 | phenyl | CH₃ | Cl  [CDCl₃] 3.85 (s, 3H, NCH₃), 4.38 (s, 2H, CH₂Cl) |
| VI-24 | 2-F-phenyl | CH₃ | Cl  [CDCl₃] 3.84 (s, 3H, NCH₃), 4.40 (s, 2H, CH₂Cl) |
| VI-25 | 2-F-phenyl | CH₃ | Cl  84-85° C. [CDCl₃] 3.81 (s, 3H, NCH₃), 4.58 (s, 2H, CH₂Cl) |

TABLE 14

The new intermediates of the general formula (VIIa) are prepared as described in Example 65a.

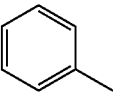

where Y = —CH$_2$—, A = ortho-phenylene, R = ethyl

| Example | Ar | R$^1$ | R$^5$ | X | Mp ° C. |
|---|---|---|---|---|---|
| VII-1 | 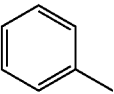 | CH$_3$ | Cl | O | 74-75° C. white crystals |
| VII-2 | 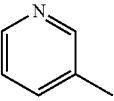 | CH$_3$ | Cl | NH | 123° C. (EtOH) white crystals |
| VII-3 | 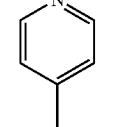 | CH$_3$ | Cl | O | 85-86° C. white crystals |
| VII-4 | 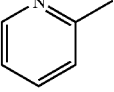 | CH$_3$ | Cl | O | 102° C. (EtOH) white crystals |
| VII-5 | 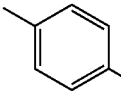 | CH$_3$ | Cl | O | 72-73° C. (EtOH) white crystals |
| VII-6 | 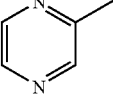 | CH$_3$ | Cl | O | 73-74° C. white crystals |
| VII-7 | 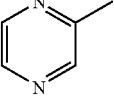 | CH$_3$ | Cl | O | 98-99° C. (EtOH) |
| VII-8 | 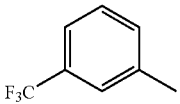 | CH$_3$ | Cl | O | 120-121° C. (EtOH) |
| VII-9 | 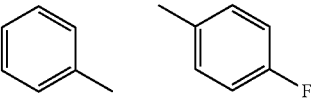 | CH$_3$ | Cl | O | 97° C. (EtOH) white crystals |
| VII-10 |  |  | Cl | O | 141-142° C. (EtOH) |

TABLE 14-continued

The new intermediates of the general formula (VIIa) are prepared as described in Example 65a.

VII

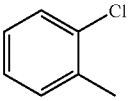

where Y = —CH₂—, A = ortho-phenylene, R = ethyl

| Example | Ar | R¹ | R⁵ | X | Mp ° C. |
|---|---|---|---|---|---|
| VII-11 | 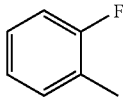 | CH₃ | Cl | O | 84-86° C. |
| VII-12 | 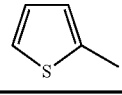 | CH₃ | Cl | O | 69-72° C. |
| VII-13 | 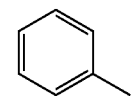 | CH₃ | Cl | O | 90-91° C. |

TABLE 15

The new intermediates of the general formula (IIa) are prepared as described in Examples 1c) (X = S) and 65b) (X = O), respectively

II

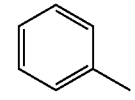

Y = —CR₂—, A = ortho-phenylene

| Example | Ar | R¹ | R⁵ | X | Mp ° C. or LCMS [M + H]⁺ |
|---|---|---|---|---|---|
| II-1 | 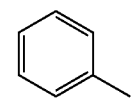 | CH₃ | Cl | S | 195-196° C. (EtOH) white crystals |
| II-2 | 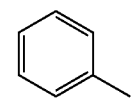 | CH₃ | H | S | 158-159° C. (EtOH) white crystals |
| II-3 | 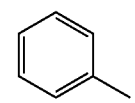 | CH₃ | Cl | NH | 192-193° C. (EtOH) hemihydrate white crystals |
| II-4 | 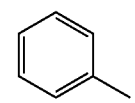 | CH₃ | Cl | O | 110-111° C. (EtOH) white crystals |

TABLE 15-continued

The new intermediates of the general formula (IIa) are prepared as described in Examples 1c) (X = S) and 65b) (X = O), respectively

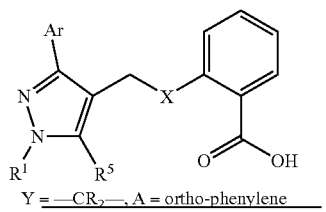

Y = —CR₂—, A = ortho-phenylene

| Example | Ar | R¹ | R⁵ | X | Mp °C. or LCMS [M + H]⁺ |
|---|---|---|---|---|---|
| II-5 | 3-pyridyl | CH₃ | Cl | S | 197-198° C. (EtOH) off-white crystals |
| II-6 | 3-pyridyl | CH₃ | Cl | O | 74-76° C. off-white crystals |
| II-7 | 4-pyridyl | CH₃ | Cl | S | >270° C. (DMF) off-white crystals |
| II-8 | 4-pyridyl | CH₃ | Cl | O | 196° C. (EtOH) off-white crystals |
| II-9 | 2-pyridyl | CH₃ | Cl | S | 218-220° C. white crystals |
| II-10 | 2-pyridyl | CH₃ | Cl | O | 127° C. off-white crystals |
| II-11 | 2,5-dichloro-4-fluorophenyl | CH₃ | Cl | S | 157-158° C. S(EtOH-iPr₂O) white crystals |
| II-12 | 3,4-dimethoxyphenyl | CH₃ | Cl | S | 163-164° C. (EtOH) white crystals |
| II-13 | 4-chlorophenyl | CH₃ | Cl | S | 225° C. (EtOH) hemihydrate white crystals |

TABLE 15-continued

The new intermediates of the general formula (IIa) are prepared as described in Examples 1c) (X = S) and 65b) (X = O), respectively

II

Y = —CR$_2$—, A = ortho-phenylene

| Example | Ar | R$^1$ | R$^5$ | X | Mp ° C. or LCMS [M + H]$^+$ |
|---|---|---|---|---|---|
| II-14 | 4-Cl-phenyl | CH$_3$ | Cl | O | 136-137° C. dihydrate white crystals |
| II-15 | pyrazin-2-yl | CH$_3$ | Cl | S | 158-159° C. (EtOH) |
| II-16 | pyrazin-2-yl | CH$_3$ | Cl | O | 146-147° C. hemihydrate off-white crystals |
| II-17 | phenyl | C$_2$H$_5$ | Cl | S | 167° C. |
| II-18 | phenyl | C$_3$H$_7$ | Cl | S | 181° C. |
| II-19 | phenyl | C$_4$H$_9$ | Cl | S | 192° C. |
| II-20 | phenyl | CH$_2$COOC$_2$H$_5$ | Cl | S | 188° C. |
| II-21 | phenyl | CH$_3$ | CH$_3$ | S | 339.2 |
| II-22 | phenyl | CH$_3$ | SCH$_3$ | S | 371.3 |
| II-23 | phenyl | CH$_3$ | Cl | SO$_2$ | 126° C. |

TABLE 15-continued

The new intermediates of the general formula (IIa) are prepared as described in Examples 1c)
(X = S) and 65b) (X = O), respectively

II

Ar—[pyrazole(N-R¹, R⁵)]—CH₂—X—[ortho-phenylene]—C(=O)OH

Y = —CR₂—, A = ortho-phenylene

| Example | Ar | R¹ | R⁵ | X | Mp ° C. or LCMS [M + H]⁺ |
|---|---|---|---|---|---|
| II-24 | 3,4-dichlorophenyl | CH₃ | Cl | O | 149-150° C. hemihydrate off-white crystals |
| II-25 | 3-(trifluoromethyl)phenyl | CH₃ | Cl | O | 144-145° C. white crystals |
| II-26 | phenyl | 4-fluorobenzyl (on N) — 4-F-C₆H₄-CH₂ as R¹? | Cl | O | 133° C. (EtOH) white crystals |
| II-27 | 2-chlorophenyl | CH₃ | Cl | O | 153-154° C. (EtOH) white crystals |
| II-28 | 2-fluorophenyl | CH₃ | Cl | O | 124-126° C. white crystals |
| II-29 | 2-thienyl | CH₃ | Cl | O | 131-132° C. |

Biological Screening Method

In vitro radioligand binding assays were used for determination of the affinities of the compounds for both the orexin-1 and orexin-2 receptors.

In the frame of hr-$^{125}$I-orexin-A radioligand competition (displacement) experiments a fixed concentration of hr-$^{125}$I-orexin-A is incubated with increasing concentrations of unlabeled test compound in the presence of highly purified plasmamembranes bearing either the human recombinant orexin-1 (hr-OX-1) or the human recombinant orexin-2 (hr-OX-2) receptors. Specific binding of hr-$^{125}$I-orexin-A to plasmamembranes is measured at each concentrations of the unlabeled compound and thus a competition curve is generated. The concentration of unlabeled compound displacing 50% of specific binding ($IC_{50}$) is calculated. In case of competitive interaction the binding affinity constant of the unlabeled compound ($K_I$) is calculated according to the Cheng-Prusoff equation ($K_I = IC_{50}/(I+L-+/K_D)$). Affinity of unlabeled compound for the receptor is equal to $1/K_I$.

In Vitro Cell Culturing and Preparation of Highly Purified Plasmamembrane Fractions Containing Orexin Receptors Culturing the Chinese hamster ovarian cells expressing human recombinant orexin-1 or orexin-2 receptor proteins (CHO-hr-OX-1 or CHO-hr-OX-2 cells) was carried out in cell culture medium (MEM medium, supplemented with 40 mg/l prolin, 20 mg/l gentamycin, 300 mg/l geneticin, 10% dialysed fetal calf serum).

We have worked out a new method for the separation of plasmamembrane fractions enriched in orexin-1 or orexin-2 receptor proteins.

Adherent cells were plated into Greiner flasks (175 cm²). 4-6 days later culture medium was removed and cells were scarped in calcium- and magnesium-free phosphate buffered saline (PBS, 20 ml/flask). The cell suspension was centrifuged at 1,000 g for 5 minutes (4° C.). The resulting pellet was resuspended and homogenized with a teflon pestle (4° C.), then layered onto a discontinous sucrose gradient and centrifuged at 105,000 g. Plasmamembrane fraction accumulated in the interface between 14 and 34% sucrose layers was separated and pelleted by a further centrifugation step at 105,000 g for 60 min (4° C.). The final pellet was resuspended in binding assay buffer and stored at −80° C. up to the day of radioligand binding experiment.

In Vitro $^{125}$I-orexin-A Binding

For $^{125}$I-orexin-A competition binding studies, aliquots of cellmembrane fractions containing either hr-orexin-1 or hr-orexin-2 receptors were incubated with $^{125}$I-orexin-A in binding assay buffer at 25° C. for 60 minutes. Nonspecific binding was defined by 1 µM hr-orexin-A in both cases.

Test compounds were dissolved at a concentration of 1 mM in dimethylsulfoxide DMSO).

Serial dilution series were prepared from stock solutions (100% DMSO) with binding assay buffer in such a way that each samples contained a final concentration of 1% of DMSO in the receptor binding reaction mixture. After the incubation, samples were filtered through Whatman GF/C glass fibre filters using a SKATRON cell harvester, and the filters were washed with 5 ml of ice-cold buffer. The radioactivity remained on the filter was counted in a gamma counter (Wallac Automatic Gamma Counter 1470 Wizard).

Abbreviations:

EGTA ethylene glycol-bis(β-aminoethyl ether)-N,N,N',N'-tetraacetic acid

Tris tris-(hydroxymethyl)aminomethane

HEPES N-2-hydroxyethylpiperazine-N'-2-ethanesulphonic acid

The invention claimed is:
1. A compound of the general formula (I)

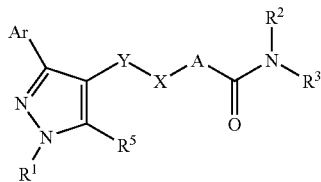

(I)

wherein:
Ar represents phenyl group or a 5- or 6-membered heteroaromatic ring containing 1-3 heteroatoms, where any of these rings may optionally be mono- or polysubstituted with halogen atom, $C_{1-4}$ alkyl group, $C_{1-4}$ alkoxy group, hydroxyl group, cyano group, trihalogenomethyl group, amino group or an amino group substituted with one or two $C_{1-4}$ alkyl groups;

Y stands —CH$_2$- group;

X stands for sulphur atom, oxygen atom, —NH-group, —N($C_{1-4}$ alkyl)group, —CH$_2$-group, —(S=O)— or —SO$_2$-group; or X and Y together represent a —CH=CH— group with cis or trans geometry;

A represents a moiety with a five- or six-membered aromatic ring which contains in ortho-, meta- or para-position two free valencies, and is optionally mono- or polysubstituted with halogen atom, $C_{1-4}$ alkyl group or $C_{1-4}$ alkoxy group; or with a partially or fully saturated five- or six-membered cycloalkyl ring optionally mono- or polysubstituted with halogen atom, $C_{1-4}$ alkyl group or $C_{1-4}$ alkoxy group; or with a heteroaromatic or partially or fully saturated heterocyclic ring which contains 1-3 heteroatoms and which is optionally mono- or polysubstituted with halogen atom, $C_{1-4}$ alkyl group or $C_{1-4}$ alkoxy group;

$R^1$ represents benzyl group, $C_{1-4}$-alkyl-, $C_{1-4}$-hydroxyalkyl-, $C_{3-8}$-alkoxycarbonylalkyl-, $C_{2-7}$-alkylcarbonyl-, $C_{2-7}$-carboxyalkyl-, aminocarbonyl-($C_{1-4}$)-alkyl, $C_{1-3}$-alkylaminocarbonyl-($C_{1-4}$)-alkyl, amino-($C_{1-4}$)-alkyl, $C_{1-3}$-alkylamino-($C_{1-4}$)-alkyl-, morpholino-($C_{1-4}$)-alkyl-, or morpholinocarbonyl-($C_{1-4}$)-alkyl group or a phenyl group, optionally substituted with one or more halogen atoms;

$R^2$ represents one of the following groups which is optionally substituted with one or more halogen atom, hydroxyl group, $C_{1-4}$ alkyl group, trihalogenomethyl-group, thio-$C_{1-4}$-alkyl group, amino group, —(C=O)—NH—$C_{1-4}$-alkyl or cycloalkyl group: phenyl group, phenylethyl group, naphthyl group, indanyl- or indenyl group, five- or six-membered heteroaromatic or partially or fully saturated cyclic group containing 1-3 identical or different heteroatoms, a group containing a bicyclic heteroaromatic moiety or a partially or fully saturated bicyclic heteroring with 1 or 2 or 3 identical or different heteroatoms;

$R^3$ stands for hydrogen atom or $C_{1-4}$ alkyl group;

or $R^3$ and $R^3$ together with the nitrogen atom to which they are attached may represent a partly or fully saturated six-membered ring optionally substituted with a substituted phenyl or benzyl group; and $R^5$ stands for halogen atom, hydrogen atom, $C_{1-4}$ alkyl group, $C_{1-4}$ thioalkyl group, or $C_{1-4}$ alkoxy group;

or a salt thereof.

2. A compound of the general formula (I)

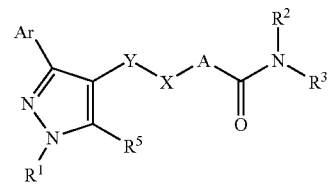

(I)

wherein:
Ar represents phenyl group or a 5- or 6-membered heteroaromatic ring containing 1-3 heteroatoms, where any of these rings may optionally be mono- or polysubstituted with halogen atom, $C_{1-4}$ alkyl group, $C_{1-4}$ alkoxy group, hydroxyl group, cyano group, trihalogenomethyl group, amino group or an amino group substituted with one or two $C_{1-4}$ alkyl group;

Y stands for —CH$_2$-group;

X stands for sulphur atom, oxygen atom, —NH-group, —N($C_{1-4}$ alkyl) group, —CH$_2$-group, —(S=O)— or —SO$_2$-group; or X and Y together represent a —CH=CH— group with cis or trans geometry;

A represents a moiety with a live- or six-membered aromatic ring which contains in ortho-, meta- or para-position two free valencies, and is optionally mono- or polysubstituted with halogen atom, $C_{1-4}$ alkyl group or $C_{1-4}$ alkoxy group; or with a partially or fully saturated five- or six-membered cycloalkyl ring optionally mono- or polysubstituted with halogen atom, $C_{1-4}$ alkyl group or $C_{1-4}$ alkoxy group; or with a heteroaromatic or partially or fully saturated heterocyclic ring which contains 1-3 heteroatoms, and is optionally mono- or polysubstituted with halogen atom, $C_{1-4}$ alkyl group or $C_{1-4}$ alkoxy group;

$R^1$ represents benzyl group, $C_{1-4}$-alkyl-, $C_{1-4}$-hydroxyalkyl-, $C_{3-8}$-alkoxycarbonylalkyl-, $C_{2-7}$-alkylcarbonyl-, $C_{2-7}$-carboxyalkyl-, aminocarbonyl-($C_{1-4}$)-alkyl, $C_{1-3}$-alkylaminocarbonyl ($C_{1-4}$)-alkyl, amino-($C_{1-4}$)-alkyl, $C_{1-3}$-alkylamino-($C_{1-4}$)-alkyl-, morpholino-($C_{1-4}$)-alkyl-, or morpholinocarbonyl-($C_{1-4}$)-alkyl group or a phenyl group, optionally substituted with one or more halogen atoms;

$R^2$ represents one of the following groups, optionally substituted with one or more halogen atom, $C_{1-4}$alkyl group, trihalogenomethyl-group, thio-$C_{1-4}$-alkyl group, amino group, —(C═O)—NH—$C_{1-4}$-alkyl or cycloalkyl group: phenyl group, phenylethyl group, naphthyl group, indanyl- or indenyl group, five- or six-membered heteroaromatic or partially or fully saturated cyclic group containing 1-3 identical or different heteroatoms, a group containing a bicyclic heteroaromatic moiety or a partially or fully saturated bicyclic heterring with 1 or 2 or 3 identical or different heteroatoms;

$R^3$ stands for hydrogen atom or $C_{1-4}$ alkyl group;

$R^2$ and $R^3$ together with the nitrogen atom to which they are attached may represent a partly or fully saturated six-membered ring optionally substituted with a substituted phenyl or benzyl group, $R^5$ stands for halogen atom, hydrogen atom, $C_{1-4}$ alkyl group, $C_{1-4}$ thioalkyl group, $C_{1-4}$ alkoxy group or a salt thereof.

3. A compound of the general formula (I) according claim 1, wherein:

Ar stands for phenyl group or a 6-membered heteroaromatic ring with 1 or 2 nitrogen atoms, where the aromatic rings may optionally be mono- or polysubstituted with halogen atom or $C_{1-4}$ alkoxy group;

Y stands for methylene group;

X stands for sulphur atom, oxygen atom, methylene group, —N(methyl)group;

A represents ortho-phenylene group or a heteroaromatic moiety containing in ortho- position two free valencies;

$R^1$ represents $C_{1-4}$-alkyl-, $C_{1-5}$-hydroxyalkyl-, $C_{3-8}$-alkoxycarbonylmethyl, $C_{2-6}$-carboxyalkyl-or methylaminocarbonyl group, or an alkylaminocarbonyl group substituted with one or two $C_{1-4}$-alkyl group;

$R^2$ represents aromatic or partially saturated bicyclic group containing 0, 1, 2 or 3 heteroatoms, optionally substituted with one or more $C_{1-4}$-alkyl group, halogen atom or amino group;

$R^3$ represents hydrogen atom; and $R^5$ represents halogen atom, $C_{1-4}$-alkyl-, or $C_{1-4}$-alkylthio group; or a salt thereof.

4. A compound of the general formula (I) according claim 1, wherein:

Ar represents a phenyl group, optionally substituted with halogen atom; or a 6-membered heteroaromatic ring with 1 or 2 nitrogen atoms, optionally substituted with halogen atom;

Y stands for methylene group;

X represents methylene group, sulphur atom, oxygen atom, or a nitrogen atom carrying a $C_{1-4}$-alkyl group;

A represents ortho-phenylene group or a heteroaromatic moiety containing in ortho-position two free valencies;

$R^1$ represents a straight or branched $C_{1-4}$-alkyl group, $C_{1-3}$-hydroxyalkyl group or $C_{3-6}$-alkoxycarbonylmethyl group;

$R^2$ represents an aromatic or partially saturated bicyclic moiety optionally substituted with $C_{1-4}$ alkyl group or halogen atom; or an aromatic or partially saturated bicyclic moiety containing 1-3 heteroatoms;

$R^3$ represents hydrogen atom; and $R^5$ represents chloro atom, methyl group or thiomethyl group; or a salt thereof.

5. A compound according claim 1, wherein said compound is:

2-(3-Phenyl-5-chloro-1-methyl-1H-pyrazol-4-ylmethylsulphanyl)-N-quinolin-3-ylbenzamide;

2-(3-Phenyl-5-chloro-1-methyl-1H-pyrazol-4-ylmethylsulplhanyl)-N-naphthalin-2-ylbenzamide;

2-(3-Phenyl-5-chloro-1-methyl-1-H-pyrazol-4-ylmethylsulphanyl)-N-quinolin-6-ylbenzamide hydrochloride;

2-(3-Phenyl-5-chloro-1-methyl-1-H-pyrazol-4-ylmethylsulphanyl)-N-indan-5-ylbenzamide;

2-(5-Chloro-1-methyl-3-pyridin-2-yl-1H-pyrazol-4-ylmethylsulphanyl)-N-naphthalin-2-ylbenzamide;

2-(5-Chloro-1-methyl-3-pyridin-2-yl-1H-pyrazol-4-ylmethylsulphanyl)-N-quinolin-3-ylbenzamide;

2-(5-Chloro-1-methyl-3-pyridin-3-yl-1H-pyrazol-4-ylmethylsulphanyl)-N-quinolin-6-ylbenzamide;

2-(5-Chloro-1-methyl-3-pyridin-3-yl-1H-pyrazol-4-ylmethylsulphanyl)-N-quinolin-3-ylbenzamide;

N-(1-Bromisoquinolin-3-yl)-2-(5-chloro-1-methyl-3-pyridin-3yl-1H-pyrazol-4-ylmethylsulphanyl)benzamide;

2-(5-Chloro-1-methyl-3-pyridin-3-yl-1H-pyrazol-4-ylmethylsulphanyl)-N-iquinolin-6-ylbenzamide;

2-(5-Chloro-1-methyl-3-pyridin-4-yl-1H-pyrazol-4-ylmethylsulphanyl)-N-naphthalin-2-ylbenzamide;

2-(5-Chloro-1-methyl-3-pyridin-4-yl-1H-pyrazol-4-ylmethylsulphanyl)-N-quinolin-3-ylbenzamide;

2-(5-Chloro-1-methyl-3-pyridin-4-yl-1H-pyrazol-4-ylmethylsulphanyl)-N-quinolin-6-ylbenzamide;

2-(5-Chloro-1-methyl-3-pyrazin-2-yl-1H-pyrazol-4-ylmethylsulphanyl)-N-quinolin-3-ylbenzamide;

2-(5-Chloro-1-methyl-3-pyridin-4-yl-1H-pyrazol-4-ylmethylsulphanyl)-N-methylisoquinolin-3-yl)benzamide;

2-(1-Ethyl-3-phenyl-5-chloro-1H-pyrazol-4-ylmethylsulphanyl)-N-quinolin-3-ylbenzamide;

2-(3-Phenyl-5-chloro-1-propyl-1H-pyrazol-4-ylmethylsulphanyl)-N-quinolin-3-ylbenzamide;

2-(1-Butyl-3-phenyl-5-chloro-4H-pyrazol-4-ylmethylsulphanyl)-N-quinolin-3-ylbenzamide;

Ethyl-{3-phenyl-5-chloro-4-[2-(quinolin-3-ylcarbamoyl)-phenylsulphanylmethyl]-1H-pyrazol-1-yl}-acetate;

2-[3-Phenyl-1-(2-hydroxyethyl)-5-chloro-1H-pyrazol-4-ylmethylsulphanyl]-N-quinolin-3-ylbenzamide;

2-(3-Phenyl-1,5-dimethyl-1H-pyrazol-4-ylmethylsulphanyl)-N-quinolin-3-ylbenzamide;

2-(3-Phenyl-1-methyl-5-methylsulphanyl-1H-pyrazol-4-ylmethylsulphanyl)-N-quinolin-3-ylbenzamide;

3-(3-Phenyl-5-chloro-1-methyl-1H-pyrazol-4-ylmethylsulphanyl)-thiophen-2-carboxylic acid naphthalin-2-ylamide;

2-(3-Phenyl-5-chloro-1-methyl-1H-pyrazol-4-ylmethoxy)-N-quinolin-3-ylbenzamide;

2-(3-Phenyl-5-chloro-1-methyl-1H-pyrazol-4-ylmethoxy)-N-naphthalin-2-ylbenzamide;

2-(5-Chloro-1-methyl-3-pyridin-3-yl-1H-pyrazol-4-ylmethoxy)-N-quinolin-3-ylbenzamide;

2-(5-Chloro-1-methyl-3-pyridin-4-yl-1H-pyrazol-4-ylmethoxy)-N-quinolin-3-ylbenzamide;

2-(5-Chloro-1-methyl-3-pyridin-2-yl-1H-pyrazol-4-ylmethoxy)-N-quinolin-3-ylbenzamide;

2-[3-(4-Fluorophenyl)-5-chloro-1-methyl-1H-pyrazol-4-ylmethoxy]-N-quinolin-3-ylbenzamide;

2-[2-(3-Phenyl-5-chloro-1-methyl-1H-pyrazol-4-yl)ethyl]-N-quinolin-3-ylbenzamide;

2-[3-(4-Fluorophenyl)-5-chloro-1-methyl-1H-pyrazol-4-ylmethoxy]-N-quinolin-3-ylbenzamide;

2-[2-(3-Phenyl-5-chloro-1-methyl-1H-pyrazol-4-yl)ethyl]-N-quinolin-3-ylbenzamide;

2-[2-(5-Chloro-1-methyl-3-pyridin-3-yl-1H-pyrazol-4-yl)ethyl]-N-quinolin-3-ylbenzamide;

2-[(3-Phenyl-5-chloro-1-methyl-1H-pyrazol-4-ylmethyl)methylamino]-N-quinolin-3-ylbenzamide;

2-(5-Chloro-1-methyl-3-pyridin-4-yl-1H-pyrazol-4-ylmethylsulphanyl)-N-(3,4-dichlorophenyl)benzamide;

2-[5-Chloro-1-methyl-3-(2-thienyl)-1H-pyrazol-4-ylmethoxy]-N-quinolin-3-ylbenzamide;

2-[(5-Chloro-1-methyl-3-pyridin-3-yl-1H-pyrazol-4-ylmethyl)methylamino]-N-quinolin-3-ylbenzamide;

2-(5-Chloro-1-methyl-3-pyridin-3-yl-1H-pyrazol-4-ylmethoxy)-N-(6,7-difluoroquinolin-3-yl)benzamide;

2-(5-Chloro-1-methyl-3-pyridazin-3-yl-1H-pyrazol-4-ylmethoxy)-N-quinolin-3-ylbenzamide; or 2-(5-Chloro-1-methyl-3-pyridazin-4-yl-1H-pyrazol-4-ylmethoxy)-N-quinolin-3-ylbenzamide; or a salt thereof.

6. A pharmaceutical composition, character in that it contains a compound of the general formula (I) according to claim 1 or salt thereof.

7. A pharmaceutical composition characterized in that it contains a compound of the general formula (I) according to claim 5 or a salt thereof.

8. A pharmaceutical composition, characterized in that it contains a compound of the general formula (I) according to claim 1 or a salt thereof, and at least one pharmaceutically acceptable excipient.

9. A compound according to claim 1, wherein each of said heteroatoms in each of said aromatic heterocycles and non-aromatic heterocycles is selected from the group consisting of nitrogen, oxygen, and sulphur;

or a salt thereof.

10. A compound according to claim 2, wherein each of said heteroatoms in each of said aromatic heterocycles and non-aromatic heterocycles is selected from the group consisting of nitrogen, oxygen, and sulphur;

or a salt thereof.

11. A compound according to claim 4, wherein each of said heteroatoms in each of said aromatic heterocycles and non-aromatic heterocycles is selected from the group consisting of nitrogen, oxygen, and sulphur;

or a salt thereof.

* * * * *

UNITED STATES PATENT AND TRADEMARK OFFICE
CERTIFICATE OF CORRECTION

PATENT NO. : 7,659,298 B2
APPLICATION NO. : 11/425583
DATED : February 9, 2010
INVENTOR(S) : Aletru et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 559 days.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,659,298 B2
APPLICATION NO. : 11/425583
DATED : February 9, 2010
INVENTOR(S) : Michel Aletru et al.

It is certified that error appears in the above-identified patent and that said Letters Patent is hereby corrected as shown below:

In column 1, line 45, delete "subgroups" and insert --sub-groups --, therefor.

In column 1, line 47, delete "orexines" and insert -- orexins --, therefor.

In column 1, line 49, delete "cells;" and insert -- cells: --, therefor.

In column 1, line 54, delete "occuring" and insert -- occurring --, therefor.

In column 2, line 6, delete "phosphiolipase" and insert -- phospholipase --, therefor.

In column 2, line 8, delete "classess" and insert -- classes --, therefor.

In column 2, line 18, before "cycle" delete ",".

In column 2, line 23, delete "stam" and insert -- stem --, therefor.

In column 2, line 23-24, delete "symphatic and parasymphatic" and insert -- sympathetic and parasympathetic --, therefor.

In column 2, line 35, delete "monoaminerg-acetylcholinerg" and insert -- monoaminergic-acetylcholinergic --, therefor.

In column 2, line 41, delete "absorbtion" and insert -- absorption --, therefor.

In column 2, line 44, delete "insuline" and insert -- insulin --, therefor.

In column 2, line 51, delete "orexin-2" and insert -- orexin-1 --, therefor.

In column 2, line 53, delete "insuline" and insert -- insulin --, therefor.

Signed and Sealed this
Thirty-first Day of May, 2011

David J. Kappos
*Director of the United States Patent and Trademark Office*

CERTIFICATE OF CORRECTION (continued)
U.S. Pat. No. 7,659,298 B2

In column 3, line 17, delete "wich" and insert -- which --, therefor.

In column 3, line 64, delete "$C_3$-s" and insert -- $C_{3-8}$ --, therefor.

In column 4, line 12, delete "nitro-en" and insert -- nitrogen --, therefor.

In column 4, line 19, delete "staight" and insert -- straight --, therefor.

In column 4, line 47, delete "beeing" and insert -- being --, therefor.

In column 5, line 22, delete "phenysulphanylmethyl]" and insert -- phenylsulphanylmethyl --, therefor.

In column 6, line 10, delete "nM" and insert -- nM. --, therefor.

In column 6, line 12, delete "According," and insert -- According --, therefor.

In column 6, line 24, delete "embodient" and insert -- embodiment --, therefor.

In column 8, line 66, delete "(H)" and insert -- (II) --, therefor.

In column 9, line 67, delete "insuline" and insert -- insulin --, therefor.

In column 10, line 5, delete "phantome" and insert -- phantom --, therefor.

In column 10, line 25, delete "parentheral" and insert -- parenteral --, therefor.

In column 10, line 27, delete "administation" and insert -- administration --, therefor.

In column 10, line 36, delete "polyethyleneglycole" and insert -- polyethyleneglycol --, therefor.

In column 10, line 46, delete "polyvinylpylpyrrolidone" and insert -- polyvinylpyrrolidone --, therefor.

In column 10, line 47, delete "lecitine." and insert -- lecithin. --, therefor.

In column 10, line 58, delete "paches" and insert -- patches --, therefor.

In column 11, line 10-11, delete "$R^3$H, $R^5$=Cl, X=S, Y=CH$_2$" and insert -- $R^3$ = H, $R^5$ = Cl, X = S, Y = CH$_2$, --, therefor.

In column 11, line 15, delete "$R^5$=Cl" and insert -- $R^5$ = Cl --, therefor.

In column 11, line 26, delete "filtrered" and insert -- filtered --, therefor.

In column 11, line 33, delete "n-ethyl" and insert -- methyl --, therefor.

In column 11, line 36, delete "Ar=Ph$_7$$R^1$=Me, $R^5$=Cl" and insert -- Ar = Ph$_7$ $R^1$ = Me, $R^5$ = Cl --, therefor.

In column 11, line 48-49, delete "$R^5$=Cl, X=S, Y=CH$_2$," and insert -- $R^5$ = Cl, X = S, Y = CH$_2$, --, therefor.

In column 12, line 17, delete "$R^3$=H, $R^5$=Cl, X=S, Y=CH$_2$" and insert -- $R^3$ = H, $R^5$ = Cl, X = S, Y = CH$_2$ --, therefor.

In column 12, line 37, delete "(m$_7$ 4H)" and insert -- (m, 4H) --, therefor.

In column 12, line 43, delete "ilbenzamide" and insert -- ylbenzamide --, therefor.

In column 12, line 44-45, delete "$R^3$=H, $R^5$=Cl, X=S, Y=CH$_2$" and insert -- $R^3$ = H, $R^5$ = Cl, X = S, Y = CH$_2$, --, therefor.

In column 12, line 51, delete "aminonaplithalene" and insert -- aminonaphthalene --, therefor.

In column 12, line 52, delete "EDC)" and insert -- (EDC) --, therefor.

In column 21, line 45, delete "1M" and insert -- 1H --, therefor.

In column 21, line 47-48, delete "$R^3$=H, $R^5$=Cl, X=S, Y=" and insert --$R^3$ = H, $R^5$ = Cl, X = S, Y = --, therefor.

In column 22, line 43, delete "0.44" and insert -- 0.44 g --, therefor.

In column 22, line 52-53, delete "$R^3$=H, $R^5$=Cl, X=S, Y=" and insert -- $R^3$ = H, $R^5$ = Cl, X = S, Y = --, therefor.

In column 22, line 59, delete "N)N" and insert -- N,N --, therefor.

In column 23, line 55, delete "$R^1$=CH$_2$CH$_2$OH," and insert --$R^1$ = CH$_2$CH$_2$OH, --, therefor.

In column 23, line 56, delete "$R^3$=H, $R^5$=Cl, X=S, Y=" and insert -- $R^3$ = H, $R^5$ = Cl, X = S, Y = --, therefor.

In column 24, line 47, delete "9911" and insert -- 99/1 --, therefor.

In column 24, line 54, delete "Ar Phenyl, $R^1$=CH$_2$COOH," and insert -- Ar = Phenyl, $R^1$ = CH$_2$COOH, --, therefor.

In column 24, line 55, delete "$R^3$=H, $R^7$=Cl, X=S, Y=" and insert -- $R^3$ = H, $R^5$ = Cl, X = S, Y = --, therefor.

In column 24, line 61, delete "(25 ml)," and insert --(25 ml). --, therefor.

CERTIFICATE OF CORRECTION (continued)

In column 24, line 66, delete "CH$_2$Cl$_{21}$MeOH" and insert -- CH$_2$Cl$_2$/MeOH --, therefor.

In column 25, line 2, delete "m.p.," and insert -- m.p.: --, therefor.

In column 25, line 9, delete "R$^1$= =" and insert -- R$^1$ = --, therefor.

In column 25, line 10-11, delete "R$^3$=H, R$^5$=Cl, X=S, Y=" and insert --R$^3$ = H, R$^5$ = Cl, X = S, Y = --, therefor.

In column 25, line 13, delete "(0.067 d" and insert -- (0.067 g --, therefor.

In column 25, line 15, delete "(0,152" and insert -- (0.152 --, therefor.

In column 25, line 23, delete "CH$_2$C$_2$Cl$_2$" and insert -- CH$_2$Cl$_2$ --, therefor.

In column 29, line 5-6, delete "R$^3$=H, R$^5$=Cl, X=O, Y=CH$_2$—" and insert -- R$^3$ = H, R$^5$ = Cl, X = O, Y = -CH$_3$- --, therefor.

In column 29, line 9, delete "R$^5$=Cl, X=O" and insert -- R$^5$ = Cl, X = O --, therefor.

In column 29, line 24, delete "CHO" and insert -- CH$_2$O --, therefor.

In column 29, line 27, delete "R$^1$ Me, R=Cl, X=O" and insert -- R$^1$ = Me, R$^5$ = Cl, X = O --, therefor.

In column 29, line 41, delete "R$^5$=Cl, X=O, Y=CH$_2$" and insert -- R$^5$ = Cl, X = O, Y = CH$_2$ --, therefor.

In column 30, line 24-25, delete "R$^3$=H, R$^5$=Cl, X=O, Y=" and insert -- R$^3$ = H, R$^5$ = Cl, X = O, Y = --, therefor.

In column 30, line 32, delete "(0.49 g" and insert -- (0.49 g, --, therefor.

In column 30, line 50-56, in Table 8, delete " 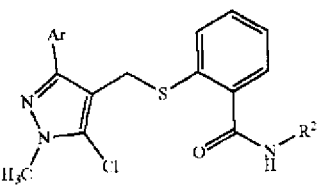 " and insert -- 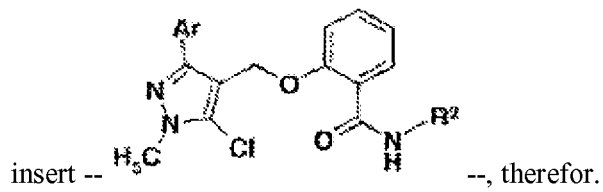 --, therefor.

In column 31, line 50-56, in Table 8, delete " 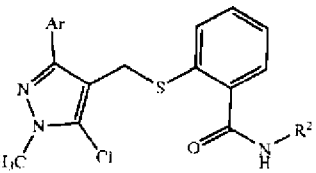 " and insert -- 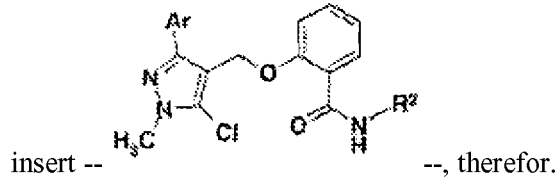 --, therefor.

In column 33, line 19, delete "B" and insert -- E --, therefor.

In column 33, line 60-61, delete "$R^3$=H, $R^5$=Cl, X=S=O, Y=" and insert
-- $R^3$ = H, $R^5$ = Cl, X = S=O, Y = --, therefor.

In column 34, line 3, delete "0.12" and insert -- 0.12 g --, therefor.

In column 34, line 10-11, delete "$R^3$H, $R^5$=Cl, X=CH=, Y=CH=," and insert
-- $R^3$ = H, $R^5$ = Cl, X = CH=, Y = CH=, --, therefor.

In column 34, line 29, delete ",g" and insert -- g, --, therefor.

In column 34, line 36, delete "ester," and insert -- ester. --, therefor.

In column 34, line 48-49, delete "dichlorometlhane" and insert -- dichloromethane --, therefor.

In column 35, line 7, delete ")" and insert -- ). --, therefor.

In column 35, line 14-15, delete "$R^3$=H, $R^5$=Cl, X=$CH_2$, Y=$CH_2$" and insert
-- $R^3$ = H, $R^5$ = Cl, X = $CH_2$, Y = $CH_2$ --, therefor.

In column 35, line 26, delete "obatined" and insert -- obtained --, therefor.

In column 35, line 53, delete "4-yl) ethyl]" and insert -- 4-yl)ethyl] --, therefor.

In column 35, line 55-56, delete "$R^3$=H, $R^5$=Cl, X=$CH_2$, Y=$CH_2$" and insert
-- $R^3$ = H, $R^5$ = Cl, X = $CH_2$, Y = $CH_2$, --, therefor.

In column 35, line 62-63, delete " tiphenylphosphine" and insert -- triphenylphosphine --, therefor.

In column 36, line 16, delete ")." and insert -- ): --, therefor.

In column 36, line 19, delete "1H)" and insert -- 1H), --, therefor.

In column 36, line 50, delete "0.25" and insert -- 0.25 g --, therefor.

In column 36, line 57-58, delete "$R^3$=H, $R^5$=Cl, X=NH, Y=CH$_2$," and insert -- $R^3$ = H, $R^5$ = Cl, X = NH, Y = CH$_2$, --, therefor.

In column 37, line 25, delete "(Ha," and insert -- (IIa --, therefor.

In column 37, line 33-34, delete "Ar Phenyl," and insert -- Ar = Phenyl --, therefor.

In column 37, line 34-35, delete "$R^3$=H, $R^5$=Cl, X=O, Y=CH$_2$, A=CH—CH," and insert -- $R^3$ = H, $R^5$ = Cl, X = O, Y = CH$_2$, A = CH$_2$CH$_2$ --, therefor.

In column 37, line 40, delete "pyrrrolidino" and insert -- pyrrolidino --, therefor.

In column 37, line 41, delete ")$_7$" and insert -- ), --, therefor.

In column 37, line 58-59, delete "$R^3$=H, $R^5$=Cl, X=—CH$_2$—, Y=—CH$_2$—, A" and insert -- $R^3$ = H, $R^5$ = Cl, X = -CH$_2$-, Y = -CH$_2$-, A= --, therefor.

In column 37, line 66, delete "m.p.;" and insert -- m.p.: --, therefor.

In column 38, line 5-6, delete "$R^3$=H, $R^5$=Cl, X=NMe, Y=" and insert --$R^3$ = H, $R^5$ = Cl, X = NMe, Y = --, therefor.

In column 38, line 9-10, delete "$R^5$==Cl, X==NMe" and insert -- $R^5$ = Cl, X = NMe --, therefor.

In column 38, line 28-29, delete "$R^5$==Cl, X==NMe" and insert -- $R^5$ = Cl, X = NMe --, therefor.

In column 38, line 40, delete "CDCl$_3$);" and insert -- CDCl$_3$): --, therefor.

In column 38, line 41, delete "3H$_7$" and insert -- 3H, --, therefor.

In column 38, line 46, delete "R=3-quinolinyl, $R^3$H, $R^5$=Cl, X=NMe, Y=CH$_2$" and insert -- $R^1$ = Me, $R^2$ = 3-quinolinyl, $R^3$ = H, $R^5$ = Cl, X = NMe, Y = CH$_2$ --, therefor.

In column 39, in Table 10/A, line 3, delete "$R^1$ = Ch$_3$ $R^3$= Cl, Y = —CH$_2$—" and insert -- $R^1$ = CH$_3$, $R^3$ = H, $R^5$ = Cl, Y = -CH$_2$- --, therefor.

In column 41-42, in Table 11, line 30, delete "3H;" and insert -- 3H); --, therefor.

In column 41-42, in Table 11, line 35, delete "3H;" and insert -- 3H); --, therefor.

In column 43-44, in Table 11, line 10, delete "2H;" and insert -- 2H); --, therefor.
In column 43-44, in Table 11, line 18, delete "3H;" and insert -- 3H); --, therefor.

In column 45-46, in Table 11, line 7, delete "5,53" and insert -- 5.53 --, therefor.

In column 53-54, in Table 13, line 24, delete "7,42" and insert -- 7.42 --, therefor.

In column 53-54, in Table 13, line 40, delete "(m 2H)" and insert -- (m, 2H) --, therefor.

In column 55-56, in Table 13, line 10-12, delete " 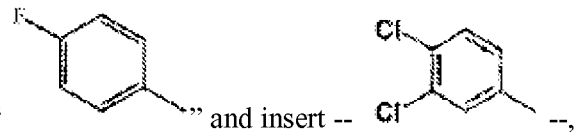 " and insert -- 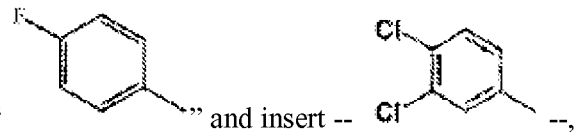 --, therefor.

In column 55-56, in Table 13, line 26-27, delete " 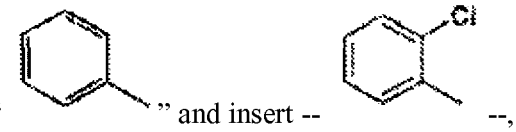 " and insert -- 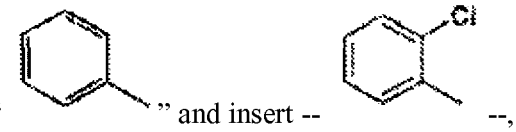 --, therefor.

In column 55-56, in Table 13, line 30-32, delete " 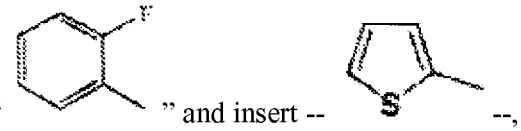 " and insert -- 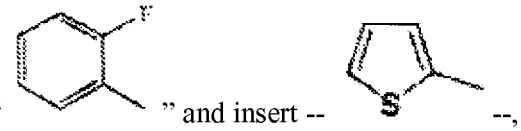 --, therefor.

In column 57-58, in Table 14, line 18-19, delete " 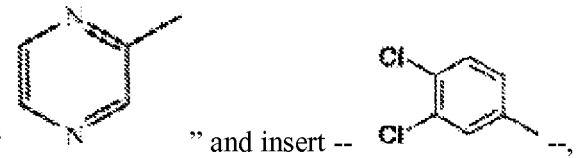 " and insert -- 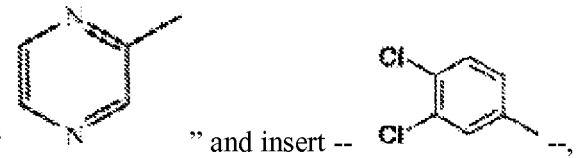 --, therefor.

In column 65, line 66, delete "($K_I$=IC$_{50}$/(I+L-+/K$_D$))." and insert -- ($K_I$ = IC$_{50}$/(I + L*/K$_D$)). --, therefor.

In column 66, line 65, delete "discontinous" and insert -- discontinuous --, therefor.

In column 67, line 13, delete "DMSO)." and insert -- (DMSO). --, therefor.

In column 67, line 54, in claim 1, after "stands" insert -- for --.

In column 68, line 25, in claim 1, delete "or R$^3$" and insert -- or R$^2$ --, therefor.

In column 68, line 59, in claim 2, delete "live-" and insert -- five- --, therefor.

In column 69, line 31, in claim 3, after "according" insert -- to --.
In column 69, line 43, in claim 3, delete "carboxyalkyl-or" and insert -- carboxyalkyl- or- --, therefor.

CERTIFICATE OF CORRECTION (continued)
U.S. Pat. No. 7,659,298 B2

In column 69, line 54, in claim 4, after "according" insert -- to --.

In column 70, line 8, in claim 5, after "according" insert -- to --.

In column 70, line 12-13, in claim 5, delete "ylmethylsulplhanyl" and insert -- ylmethylsulphanyl- --, therefor.

In column 70, line 14, in claim 5, delete "1-H" and insert -- 1H --, therefor.

In column 70, line 16, in claim 5, delete "1-H" and insert -- 1H --, therefor.

In column 70, line 26, in claim 5, delete "Bromisoquinolin" and insert -- Bromoisoquinolin --, therefor.

In column 70, line 27, in claim 5, delete "3yl" and insert -- 3-yl --, therefor.

In column 70, line 29, in claim 5, delete "iquinolin" and insert -- isoquinolin --, therefor.

In column 70, line 39, in claim 5, delete "-N-" and insert -- -N-(1- --, therefor.

In column 70, line 44, in claim 5, delete "4H" and insert -- 1H --, therefor.

In column 72, line 1, in claim 6, delete "character" and insert -- characterized --, therefor.